United States Patent
Rothberg et al.

(10) Patent No.: US 10,628,932 B2
(45) Date of Patent: Apr. 21, 2020

(54) QUALITY INDICATORS FOR COLLECTION OF AND AUTOMATED MEASUREMENT ON ULTRASOUND IMAGES

(71) Applicant: Butterfly Network, Inc., Guilford, CT (US)

(72) Inventors: Alex Rothberg, New York, NY (US); Igor Lovchinsky, New York, NY (US); Jimmy Jia, New York, NY (US); Tomer Gafner, Forest Hills, NY (US); Matthew de Jonge, Brooklyn, NY (US); Jonathan M. Rothberg, Guilford, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/172,076

(22) Filed: Oct. 26, 2018

(65) Prior Publication Data

US 2019/0130554 A1    May 2, 2019

Related U.S. Application Data

(60) Provisional application No. 62/578,260, filed on Oct. 27, 2017.

(51) Int. Cl.
*G06T 7/00* (2017.01)
*G01S 17/00* (2020.01)
*A61B 8/08* (2006.01)

(52) U.S. Cl.
CPC ............ *G06T 7/0002* (2013.01); *G01S 17/00* (2013.01); *A61B 8/0883* (2013.01); *A61B 8/5215* (2013.01);

(Continued)

(58) Field of Classification Search
CPC ......... G06T 7/0002; G06T 2207/10132; G06T 2207/20081; G06T 2207/30168;
(Continued)

(56) References Cited

U.S. PATENT DOCUMENTS 6,112,234 A    8/2000  Leiper
6,370,480 B1 *  4/2002  Gupta ..................... A61B 8/00
                                                      702/39

(Continued)

FOREIGN PATENT DOCUMENTS

WO    WO 2014/155272 A1    10/2014
WO    WO 2017/108667 A1     6/2017
(Continued)

OTHER PUBLICATIONS

Invitation to Pay Additional Fees dated Dec. 26, 2018 in connection with International Application No. PCT/US2018/057722.
(Continued)

*Primary Examiner* — Xuemei G Chen
(74) *Attorney, Agent, or Firm* — Wolf, Greenfield & Sacks, P.C.

(57) ABSTRACT

Aspects of the technology described herein relate to techniques for calculating, during imaging, a quality of a sequence of images collected during the imaging. Calculating the quality of the sequence of images may include calculating a probability that a medical professional would use a given image for clinical evaluation and a confidence that an automated analysis segmentation performed on the given image is correct. Techniques described herein also include receiving a trigger to perform an automatic measurement on a sequence of images, calculating a quality of the sequence of images, determining whether the quality of the sequence of images exceeds a threshold quality, and performing the automatic measurement on the sequence of
(Continued)

images based on determining that the quality of the sequence of images exceeds the threshold quality.

19 Claims, 24 Drawing Sheets

(52) U.S. Cl.
CPC ............... *G06T 2207/10016* (2013.01); *G06T 2207/10132* (2013.01); *G06T 2207/20076* (2013.01); *G06T 2207/20081* (2013.01); *G06T 2207/30168* (2013.01)

(58) Field of Classification Search
CPC . G06T 2207/10016; G06T 2207/20076; A61B 8/00; G01S 17/00
See application file for complete search history.

(56) References Cited

U.S. PATENT DOCUMENTS

| | | | |
|---|---|---|---|
| 8,081,227 B1 | 12/2011 | Kim et al. | |
| 8,235,905 B2* | 8/2012 | Lin | A61B 8/00 600/443 |
| 8,581,987 B1 | 11/2013 | Chu et al. | |
| 8,891,881 B2 | 11/2014 | Gupta et al. | |
| 9,734,626 B2* | 8/2017 | Jago | A61B 8/0866 |
| 9,760,830 B2* | 9/2017 | Becker | A61B 6/481 |
| 9,918,701 B2* | 3/2018 | Hedlund | A61B 6/487 |
| 10,127,659 B2* | 11/2018 | Hsieh | G06F 19/00 |
| 2005/0134942 A1* | 6/2005 | Kondo | G06T 3/4007 358/479 |
| 2009/0073266 A1 | 3/2009 | Abdellaziz Trimeche et al. | |
| 2009/0116713 A1* | 5/2009 | Yan | G06K 9/4619 382/128 |
| 2010/0087746 A1 | 4/2010 | Radzievsky et al. | |
| 2011/0055447 A1 | 3/2011 | Costa | |
| 2011/0109459 A1* | 5/2011 | Poeze | A61B 5/14551 340/573.1 |
| 2012/0065510 A1* | 3/2012 | Snare | A61B 8/14 600/443 |
| 2013/0141602 A1* | 6/2013 | Kuriyama | H04N 5/23232 348/208.6 |
| 2013/0242116 A1* | 9/2013 | Fujii | H04N 17/00 348/180 |
| 2014/0133764 A1* | 5/2014 | Hong | G06K 9/00221 382/224 |
| 2015/0036888 A1* | 2/2015 | Weisenburger | G06T 7/80 382/107 |
| 2017/0322308 A1* | 11/2017 | Loupas | A61B 8/485 |
| 2017/0360399 A1 | 12/2017 | Rothberg et al. | |
| 2018/0061054 A1* | 3/2018 | Abraham | G06T 7/60 |
| 2018/0153505 A1 | 6/2018 | Cadieu et al. | |
| 2018/0161010 A1* | 6/2018 | Choi | A61B 8/5215 |
| 2018/0185011 A1* | 7/2018 | Daft | A61B 8/145 |
| 2018/0218755 A1* | 8/2018 | Kawaguchi | H04N 5/772 |
| 2018/0310920 A1 | 11/2018 | Specht et al. | |
| 2019/0015076 A1* | 1/2019 | Rouet | A61B 8/4245 |
| 2019/0035047 A1* | 1/2019 | Lim | G06T 1/20 |
| 2019/0114064 A1* | 4/2019 | Monibi | G06F 3/04855 |
| 2019/0117186 A1* | 4/2019 | Klinder | G06T 7/174 |
| 2019/0117190 A1 | 4/2019 | Djajadiningrat et al. | |
| 2019/0125298 A1* | 5/2019 | Abolmaesumi | A61B 8/0883 |
| 2019/0266716 A1 | 8/2019 | Rothberg et al. | |

FOREIGN PATENT DOCUMENTS

| | | |
|---|---|---|
| WO | WO 2017/181288 A1 | 10/2017 |
| WO | WO 2017/222970 A1 | 12/2017 |
| WO | WO 2019/046521 A1 | 3/2019 |

OTHER PUBLICATIONS

International Search Report and Written Opinion dated Feb. 15, 2019 in connection with International Application No. PCT/US2018/057722.

\* cited by examiner

QUALITY INDICATORS FOR COLLECTION OF AND AUTOMATED MEASUREMENT ON ULTRASOUND IMAGES

CROSS-REFERENCE TO RELATED APPLICATIONS

This application claims the benefit under 35 U.S.C. § 119(e) of U.S. Provisional Application Ser. No. 62/578,260, titled "QUALITY INDICATORS FOR COLLECTION OF AND AUTOMATED MEASUREMENT ON ULTRASOUND IMAGES," filed on Oct. 27, 2017, which is incorporated herein by reference in its entirety.

FIELD

Generally, the aspects of the technology described herein relate to ultrasound systems. Some aspects relate to techniques for generating an indicator of the quality of a sequence of images.

BACKGROUND

Conventional ultrasound systems are large, complex, and expensive systems that are typically used in large medical facilities (such as a hospital) and are operated by medical professionals that are experienced with these systems, such as ultrasound technicians. Ultrasound technicians typically undergo years of hands-on training to learn how to properly use the ultrasound imaging system. For example, an ultrasound technician may learn how to appropriately position an ultrasound device on a subject to capture an ultrasound image in various anatomical views. Further, an ultrasound technician may learn how to read captured ultrasound images to infer medical information about the patient.

SUMMARY

According to one aspect, a method includes calculating, during imaging, using a computing device in communication with an ultrasound device, a quality of a sequence of images collected by the ultrasound device during the imaging. In some embodiments, the method includes generating for display, during the imaging, an indicator of the quality of the sequence of images. In some embodiments, the method further includes receiving a newest image collected during the imaging; removing an oldest image from the sequence of images and adding the newest image to the sequence of images to form a new sequence of images; calculating, during the imaging, a quality of the new sequence of images; and generating for display, during the imaging, an indicator of the quality of the new sequence of images to replace the indicator of the quality of the sequence of images.

In some embodiments, the method further includes generating for display instructions for moving the ultrasound device performing the imaging. In some embodiments, generating for display the instructions for moving the ultrasound device performing the imaging includes generating for display the instructions simultaneously with generating for display the indicator of the quality of the sequence of images. In some embodiments, generating for display the instructions for moving the ultrasound device performing the imaging includes generating for display the instructions prior to generating for display the indicator of the quality of the sequence of images.

In some embodiments, the sequence of images includes a sequence of images collected during a fixed period of time prior to calculating the quality of the sequence of the images. In some embodiments, the sequence of images includes a fixed number of images collected prior to calculating the quality of the sequence of the images.

In some embodiments, calculating the quality of the sequence of images includes analyzing the sequence of images using deep learning techniques. In some embodiments, calculating the quality of the images includes providing at least one image in the sequence of images as an input to a statistical model. In some embodiments, calculating the quality of the images includes using the statistical model to obtain an output that is indicative of the quality of the at least one image.

In some embodiments, the method further includes generating for display, during the imaging, an indicator of an acceptability of the sequence of images. In some embodiments, generating for display the indicator of the quality of the sequence of images includes generating for display a frame having a first end and a second end and generating for display a bar within the frame that extends from the first end towards the second, where a length of the bar relative to the frame is proportional to the quality of the sequence of the images.

In some embodiments, the method further includes generating for display, during the imaging, an indicator of an acceptability of the sequence of images, where the indicator of the acceptability of the sequence of images includes an indicator of a threshold quality such that a distance from the first end to the indicator of the threshold quality relative to the length of the bar is proportional to the threshold quality.

In some embodiments, the method further includes: storing one or more images in the sequence of images in a volatile memory; deleting an oldest image from the one or more images stored in the volatile memory; adding a newest image to the one or more images stored in the volatile memory; determining that a quality of the one or more images stored in the volatile memory exceeds a threshold quality; and based on determining that the quality of the one or more images stored in the volatile memory exceeds the threshold quality, transferring the one or more images stored in the volatile memory from the volatile memory to a non-volatile memory. In some embodiments calculating the quality of the sequence of images includes calculating a quality of each respective image in the sequence of images and calculating an arithmetic mean of the quality of each respective image in the sequence of images to produce the quality of the sequence of images. In some embodiments, calculating the quality of each respective image in the sequence of images includes, for each respective image in the sequence of images, calculating a clinical use metric including a probability that a medical professional would use the respective image for clinical evaluation, calculating an automated analysis metric including a quality of an automated analysis performed on the respective image, and calculating a geometric mean of the clinical use metric and the automated analysis metric to produce the quality of the respective image.

According to another aspect, a method for performing automatic measurements on a sequence of images collected by an ultrasound device includes: receiving, using a computing device, a trigger to perform an automatic measurement on the sequence of images; calculating a quality of the sequence of images; determining whether the quality of the sequence of images exceeds a threshold quality; and based on determining that the quality of the sequence of images exceeds the threshold quality, performing the automatic measurement on the sequence of images.

In some embodiments, the method further includes, based on determining that the quality of the sequence of images does not exceed the threshold quality, generating for display an indicator that the quality of the sequence of images does not exceed the threshold quality. In some embodiments, the method further includes, based on determining that the quality of the sequence of images does not exceed the threshold quality, entering a manual mode in which an operator may perform a manual measurement on the sequence of images.

In some embodiments, calculating the quality of the sequence of images includes calculating a quality of each respective image in the sequence of images to produce a plurality of qualities and calculating a fixed percentile of the plurality of qualities to produce the quality of the sequence of images. In some embodiments, calculating the quality of each respective image in the sequence of images includes, for each respective image in the sequence of images, calculating a clinical use metric including a probability that a medical professional would use the respective image for clinical evaluation, calculating an automated analysis metric including a quality of an automated analysis performed on the respective image, and calculating a geometric mean of the clinical use metric and the automated analysis metric to produce the quality of the respective image. In some embodiments, the automatic measurement includes automatic measurement of an ejection fraction, and calculating the quality of the sequence of images includes: calculating a first quality including a minimum of a first plurality of qualities of a first plurality of images, where the first plurality of images includes a first image corresponding to end-diastole and one or more images that are temporarily adjacent to the first image in the sequence of images; calculating a second quality including a minimum of a second plurality of qualities of a second plurality of images, where the second plurality of images includes a second image corresponding to end-systole and one or more images that are temporarily adjacent to the second image in the sequence of images; calculating a quality of each respective image in the sequence of images to produce a third plurality of qualities; calculating a fixed percentile of the third plurality of qualities to produce a third quality; and selecting the quality of the sequence of images as a minimum of the first quality, the second quality, and the third quality.

Some aspects include at least one non-transitory computer-readable storage medium storing processor-executable instructions that, when executed by at least one processor, cause the at least one processor to perform the above aspects and embodiments. Some aspects include an apparatus having a computing device configured to perform the above aspects and embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
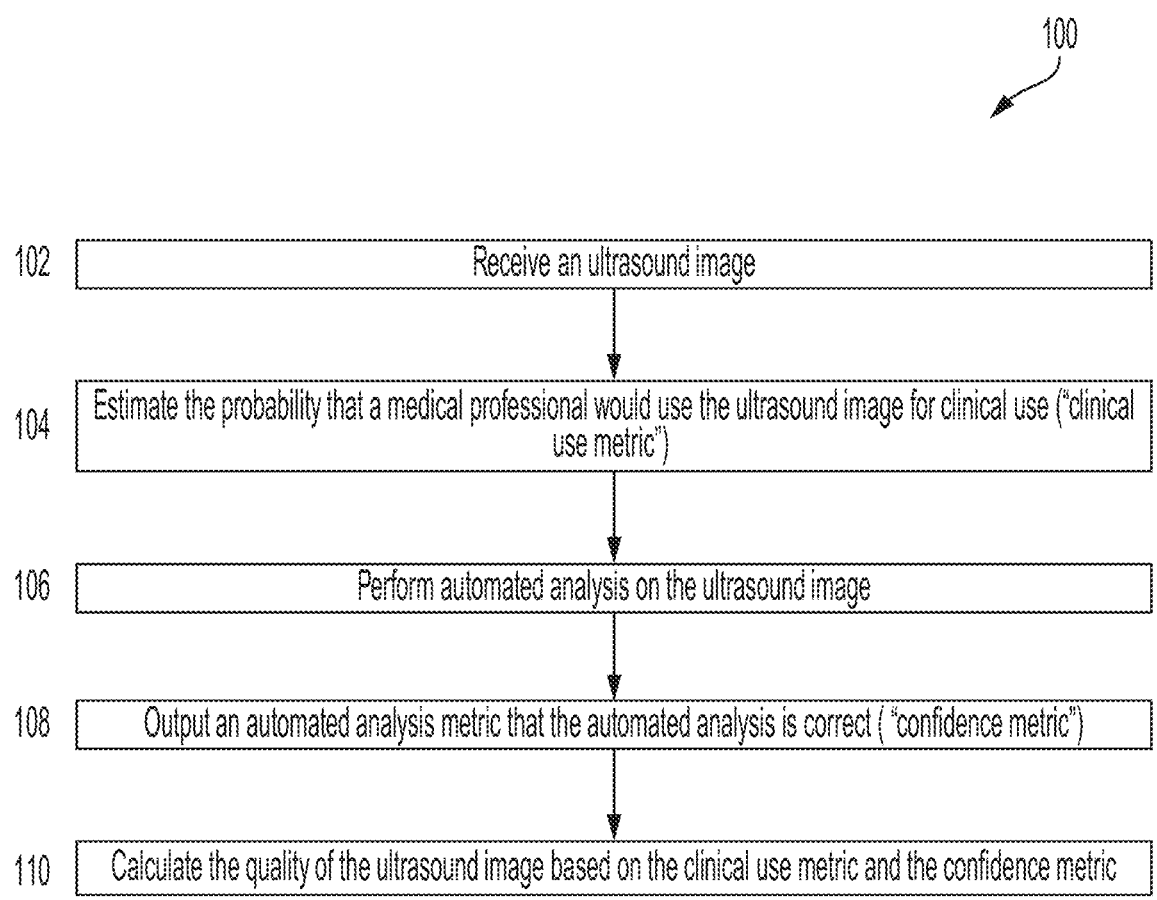
FIG. 1 illustrates an example process for calculating the quality of an ultrasound image, in accordance with certain embodiments described herein.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application) and published as U.S. Pat. Pub. 2017/0360397 A1, which is incorporated by reference herein in its entirety. The reduced cost and increased portability of these new ultrasound devices may make them significantly more accessible to the general public than conventional ultrasound devices. At the same time, advances in artificial intelligence technology have enabled performance of automatic measurements on ultrasound images, potentially obviating the need for operators to have the required knowledge for manually performing such measurements. Aspects of such automatic measurements are described in U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1, which is incorporated by reference herein in its entirety.

However, the inventors have recognized that people in the general populace who could make use of such devices have little to no training for how to use them. For example, an operator of such an ultrasound imaging device may not be able to evaluate the quality of images collected during imaging and may therefore not know how suitable collected images are for use in performing automatic measurements (e.g., automatically measuring ejection fraction). Accordingly, the inventors have recognized that it may be helpful to calculate and generate for display an indicator of the quality of a sequence of images collected by an ultrasound device in real-time as the images are collected. An operator performing imaging with an ultrasound device may monitor the quality indicator, as indicated by the length and/or color of the quality indicator, in order to move the ultrasound device to a location on the subject from which images can be collected that have a maximum quality relative to images collected from other locations. The operator may use "hill climbing" for moving the ultrasound device based on the quality indicator, in which the operator moves the ultrasound device in a direction that causes the quality to rise, and once the quality begins to fall, the operator moves the ultrasound device back in the opposite direction to the location where the maximum quality along the direction occurred. The operator may then move the ultrasound device in a different direction from that location to further attempt to maximize the quality.

The inventors have further recognized that an operator of an ultrasound device may not know whether a collected sequence of images is of sufficient quality for use in automatically performing measurements (e.g., in the case of images collected from the heart, whether the maximum quality is sufficient for accurately measuring ejection fraction). For example, as discussed above, an operator may use a quality indicator to move an ultrasound device to a location on the subject from which images can be collected that have a maximum quality relative to images collected from other locations. However, the operator may not know whether that maximum quality is sufficient for automatically performing measurements (e.g., accurately measuring ejection fraction). For example, the ultrasound imaging device may be positioned properly, but settings of the ultrasound imaging device may be incorrect, or impedance matching coupling between the ultrasound imaging device and the subject may be poor, or the subject may be moving, etc. Accordingly, the inventors have recognized that it may helpful to generate for display an indicator of the acceptability of the sequence of images for automatically performing measurements.

Typically, an ultrasound imaging system will display images being collected but not save images to memory (e.g., non-volatile memory) until an operator initiates the saving to memory. Saving images to memory may be used to perform automated measurements (e.g., ejection fraction calculation) using the saved images. For example, the computing device may automatically perform measurements on the saved images using artificial intelligence/deep learning. The quality indicator and the acceptability indicator may be used by the operator to determine when to begin to save images to memory. For example, upon moving an ultrasound device to a location on the subject from which images can be collected that have a maximum quality relative to images collected from other locations (as indicated by the quality indicator), the operator may begin to save images being collected from that location to memory (e.g., by pressing a record button). As another example, upon moving the ultrasound device to a location on the subject from which images can be collected that have an acceptably high quality (as indicated by the acceptability indicator), the operator may begin to save images being collected from that location to memory. In such embodiments, the quality of previous images collected at a location, as indicated by the quality indicator and/or the acceptability indicator, may inform a user when to begin to save further images collected at that location.

The inventors have further recognized that even if an operator initiates saving of images to memory (e.g., non-volatile memory) based on monitoring the quality indicator and/or acceptability indicator for a previously collected sequence of images, the images that are saved may be low quality and/or unacceptable for automatically performing measurements (e.g., automatically measuring ejection fraction). For example, after initiating saving of images to memory, the operator may accidentally remove the ultrasound probe from the subject. Accordingly, in some embodiments, upon an operator saving a sequence of images for automatic measurement (e.g., automatic measurement of ejection fraction) based on the sequence of images, a quality of the saved sequence of images may be calculated. If the quality is above a threshold quality (e.g., 50% on a scale of 0% to 100%), automatic measurement based on the sequence of images may proceed. If the quality is below the threshold quality, an error may be displayed indicating that automatic measurement will not proceed. By not performing automatic measurements on sequences of images if the condition discussed above is not met, the system may avoid presenting automatic measurements calculated on low quality sequences of images that may be clinically irrelevant.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 2:
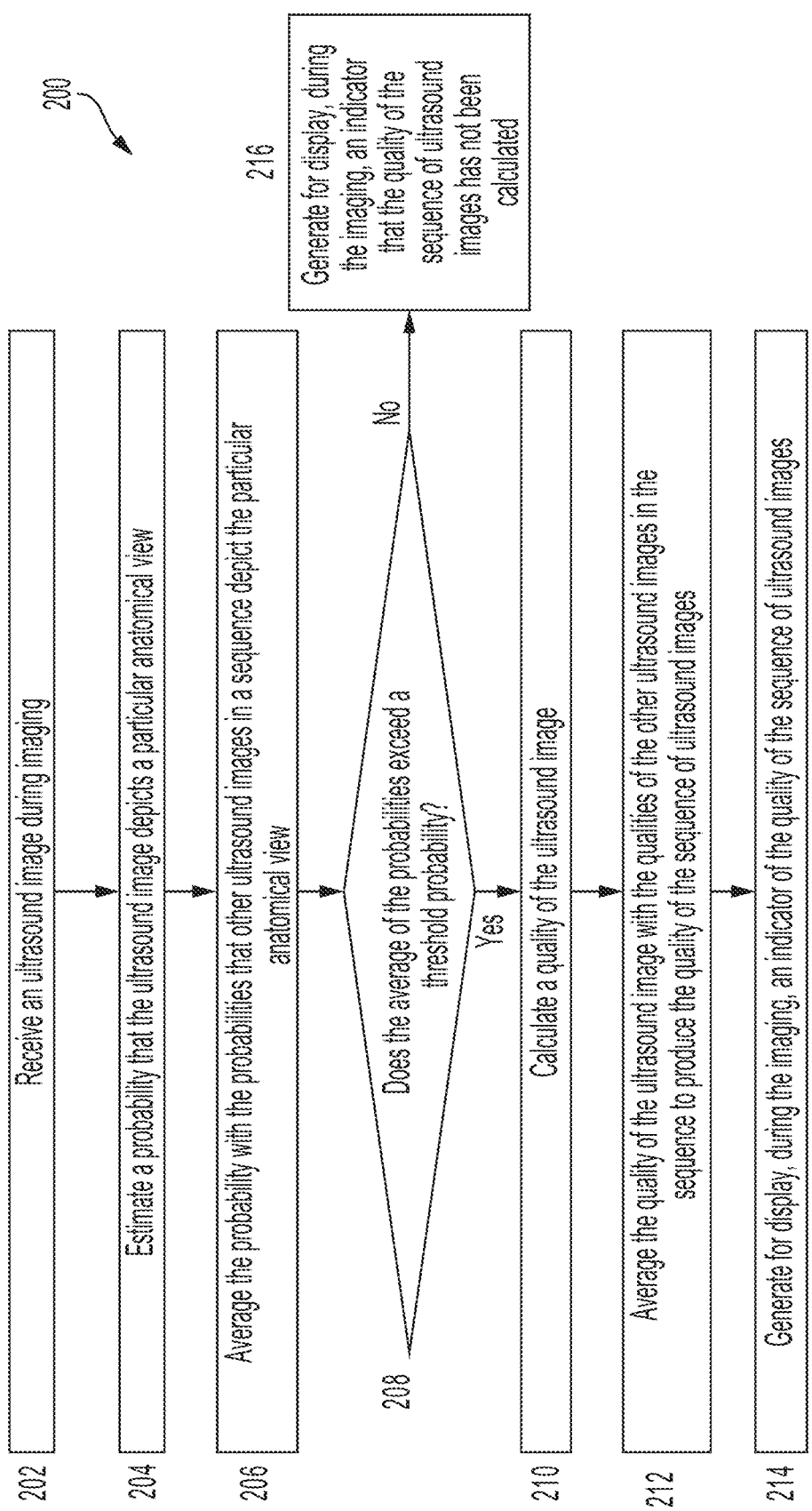
FIG. 2 illustrates an example process for calculating and displaying a live quality of a sequence of ultrasound images, in accordance with certain embodiments described herein.
Figure 3:
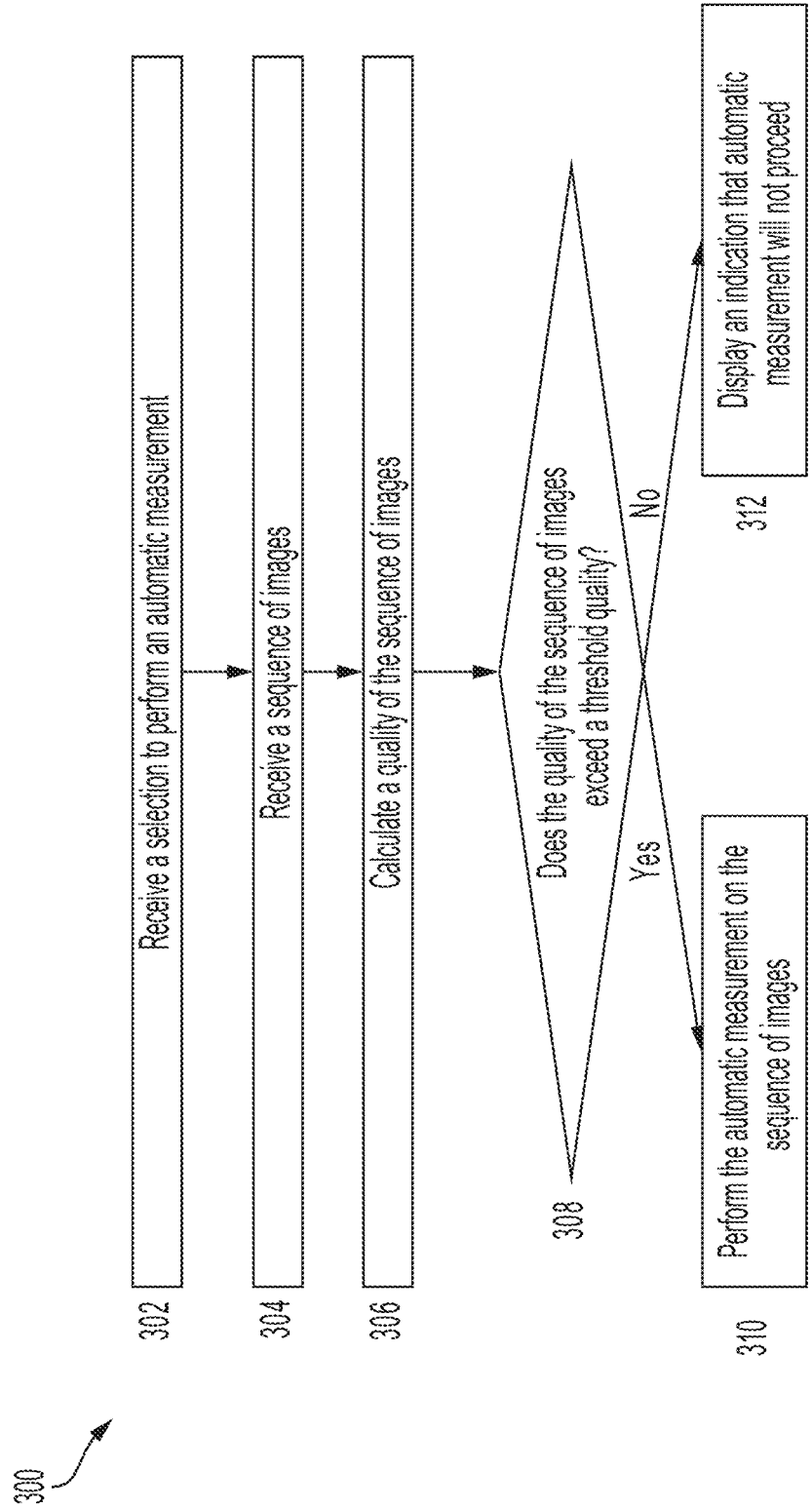
FIG. 3 illustrates an example process for performing an automatic measurement on a sequence of ultrasound images based on calculating the offline quality of the sequence of ultrasound images, in accordance with certain embodiments described herein.

The processes 100, 200, and 300, which are depicted in FIGS. 1-3, are performed by a computing device in operative communication with an ultrasound device. Further description of computing devices and ultrasound devices may be found below with reference to FIGS. 22-23.

FIG. 1 illustrates an example process 100 for calculating the quality of an ultrasound image, in accordance with certain embodiments described herein. The process 100 begins with act 102. In act 102, the computing device receives an ultrasound image. In some embodiments, the computing device may receive raw acoustical data from the ultrasound device and generate the ultrasound image based on the raw acoustical data. In some embodiments, the computing device may receive scan lines from the ultrasound device and generate the ultrasound image based on the scan lines. In some embodiments, rather than the computing device generating the ultrasound image, the ultrasound device may generate the ultrasound image based on the first ultrasound data and transmit the ultrasound image to the computing device. The ultrasound image may be generated based on the most recently collected ultrasound data. In some embodiments, the computing device may retrieve the ultrasound image from memory. The process 102 proceeds from act 102 to act 104.

In act 104, the computing device estimates the probability (between 0% and 100%) that a medical professional would use the image for clinical use, such as for measuring ejection fraction (referred to for simplicity as "clinical use metric"). In some embodiments, the computing device may use a statistical model to estimate this probability. To train the statistical model to estimate this probability, the statistical model may be trained with images labeled with an indication of whether a medical professional would use the images for clinical evaluation or not. Statistical models referred to herein may include a convolutional neural network, a fully connected neural network, a recurrent neural network (e.g., a long short-term memory (LSTM) recurrent neural network), a random forest, a support vector machine, a linear classifier, and/or any other statistical model. As referred to herein, a "statistical model" may include one or more statistical models. The process 100 proceeds from act 104 to act 106.

In act 106, the computing device performs an automated analysis on the image. In some embodiments, the computing device may use a statistical model to perform the automated analysis. In some embodiments, the automated analysis may be localization of keypoints in the image. For example, the automated analysis may include localization of two keypoints (that have been defined by the medical community) on the anterior and posterior wall of the left ventricle in images showing the parasternal long axis of the heart for the purpose of automatically calculating ejection fraction. As another example, the automated analysis may include localization two keypoints that are base points of the mitral valve for the purpose of automatically calculating ejection fraction using Simpson's method. To train the statistical model to perform keypoint localization on images, the statistical model may be trained with images that have been manually labeled with the keypoints. In some embodiments, the automated analysis may be segmentation of the image (e.g., delineating foreground vs. background). For example, the automated analysis may be segmentation of the left ventricle from the rest of the image in an image showing the apical four chamber view of the heart for the purpose of calculating ejection fraction. To train the statistical model to perform segmentation on images, the statistical model may be trained with images that have been manually segmented. The process 100 proceeds from act 106 to act 108.

In act 108, the computing device outputs a quality (between 0% and 100%) of the automated analysis (referred to for simplicity as "automated analysis metric"). In some embodiments, the computing device may use a statistical model to output the automated analysis metric. When the automated analysis includes keypoint localization, the automated analysis metric may include a metric quantifying the quality of the keypoint localization based on the confidence of the statistical model in the keypoint localization. The statistical model may output, for a given inputted ultrasound image and for each keypoint, a heatmap indicating the probability that the keypoint is located at a particular location, where the peak of the heatmap corresponds to the statistical model's prediction for the location of a keypoint. The quality of the keypoint localization may be quantified as the difference between the maximum and minimum values of a heatmap. When the statistical model is confident in the localization of the keypoint, the heatmap may be highly peaked, leading to a large difference between the maximum and minimum values of a heatmap. When the statistical model is not confident in the localization of the keypoint, the heatmaps may be spread out, leading to a small difference between the maximum and minimum values of a heatmap. For example, when the automated analysis includes localization of two keypoints on the anterior and posterior wall of the left ventricle in images showing the parasternal long axis of the heart for the purpose of calculating ejection fraction, the automated analysis metric may be based, at least in part, on the difference between the maximum and minimum values of the heatmap outputted by the statistical model for each keypoint. As another example, when the automated analysis includes localization of two keypoints that are base points of the mitral valve in images showing the apical four-chamber view of the heart for the purpose of calculating ejection fraction, the automated analysis metric may be based, at least in part, on the difference between the maximum and minimum values of the heatmap outputted by the statistical model for each keypoint. In some embodiments, the quality of the keypoint localization may be quantified as the maximum value of a heatmap.

When the automated analysis includes segmentation, the automated analysis metric may include several metrics quantifying quality of the segmentation. In some embodiments, segmenting an image may include generating a segmentation mask, where the mask includes a pixel array that is the same size of the image. Each pixel of the segmentation mask may have a value ranging from 0 to 1. The statistical model may have high confidence that pixels having values closer to 0 are not part of the segmented portion and have high confidence that pixels having values closer to 1 are part of the segmented portion. The statistical model may not have high confidence about whether pixels having values closer to 0.5 are part of or not part of the segmented portion. The statistical model may consider pixels having values greater than 0.5 to be part of the segmented portion and consider pixels having values less than 0.5 to not be part of the segmented portion. (Whether pixels having a value of exactly 0.5 are or are not considered part of the segmented portion may vary between embodiments.) One metric quantifying quality of the segmentation may be the Shannon entropy of the segmentation mask, which may measure how many pixels are near 0.5 versus how many pixels are near 0 or 1. Thus, this metric may quantify how confident the statistical model is regarding the segmentation. A second metric quantifying quality of the segmentation may be the area of the segmented region. A third metric quantifying quality of the segmentation may be circularity of the segmented region. The circularity of the segmented region may be computed as (segmentation_contour_length)

^2/(4*pi*segmentation_area), where segmentation_contour_length is the length of a contour surrounding the segmented region and segmentation_area is the area of the segmented region. A circle may have a circularity metric of 1 and other shapes may have circularity metrics that are greater than 1. These metrics may be used to calculate, at least in part, the automated analysis metric when the automated analysis includes segmentation of the left ventricle in images showing the apical four-chamber view of the heart for the purpose of calculating ejection fraction. In other words, the automated analysis metric for images showing the apical four-chamber view of the heart may be based, at least in part, both on the segmentation and the keypoint localization quality metrics described above. Multiple such metrics may be combined using logistic regression to produce a single automated analysis metric. The process 100 proceeds from act 108 to act 110.

In act 110, the computing device calculates the quality of the image based on the clinical use metric and the automated analysis metric. In some embodiments, the computing device may calculate the mean of the clinical use metric and the automated analysis metric. In some embodiments, the mean may be the geometric mean. Using a geometric mean may help to ensure that the calculated quality is not high if either of the clinical use or automated analysis metrics is low. In some embodiments, the mean may be the arithmetic mean.

In some embodiments, only the clinical use metric may be used to calculate the quality of the ultrasound image. In other words, acts 106, 108, and 110 may be absent. In some embodiments, only the automated analysis metric may be used to calculate the quality of the ultrasound image. In other words, acts 104 and 110 may be absent. In some embodiments, other combinations of the acts of the process 100 may be absent. In some embodiments, other additional metrics may be used to calculate the quality of the ultrasound image, or a different metric or set of metrics may be used.

FIG. 2 illustrates an example process 200 for calculating and displaying a live quality of a sequence of ultrasound images, in accordance with certain embodiments described herein. The live quality may be calculated in real-time during imaging, as the images are collected. The process 200 begins with act 202. In act 202, the computing device receives an ultrasound image during imaging with the ultrasound device. In some embodiments, the computing device may receive raw acoustical data from the ultrasound device and generate the ultrasound image based on the raw acoustical data. In some embodiments, the computing device may receive scan lines from the ultrasound device and generate the ultrasound image based on the scan lines. In some embodiments, rather than the computing device generating the ultrasound image, the ultrasound device may generate the ultrasound image based on the first ultrasound data and transmit the ultrasound image to the computing device. The ultrasound image may be generated based on the most recently collected ultrasound data. The process 200 proceeds from act 202 to act 204.

In act 204, the computing device estimates a probability (e.g., between 0% and 100%) that the ultrasound image depicts a particular anatomical view (e.g., apical four-chamber view of the heart, parasternal long axis view of the heart, etc.). As will be described below, a statistical model may be trained to calculate the quality of an ultrasound image depicting a particular anatomical view. If an ultrasound image that does not depict the anatomical view is inputted to the statistical model, the statistical model may not output a meaningful quality, as the statistical model may not have been trained to process ultrasound images depicting other anatomical views. For example, the statistical model may incorrectly output a high quality for such an ultrasound image, even though the ultrasound image is not a high-quality ultrasound image depicting the anatomical view. Thus, in some embodiments, the computing device may not calculate the quality of an ultrasound image unless the statistical model first determines that the ultrasound image depicts the anatomical view for which the statistical model is trained to output the quality. To estimate a probability that the ultrasound image depicts a particular anatomical view, a statistical model may be trained on ultrasound images that have been manually labeled with the anatomical views they depict. The process 200 proceeds from act 204 to act 206.

In act 206, the computing device averages the probability estimated in act 204 with the probabilities that other ultrasound images in a sequence depict the particular anatomical view. The probabilities associated with the other ultrasound images in the sequence may, for example, also be estimated using the techniques described in act 204. In some embodiments, the ultrasound device may average the probabilities of the images using the arithmetic mean. The sequence of images may constitute the sequence of images previously collected during imaging, where the sequence of images constitutes a fixed number of images (e.g., the previous 10 images collected) or the images collected over a fixed period of time (e.g., the images collected over the previous 2 seconds). The process proceeds from act 206 to act 208.

In act 208, the computing device determines whether the average of the probabilities calculated in act 206 exceeds (or in some embodiments, exceeds or is equal to) a threshold probability (e.g., 50%). If the average of the probabilities calculated in act 206 exceeds the threshold probability, this may indicate that the sequence of images depicts the particular anatomical view and calculation of the quality of the sequence of images may proceed, and the process 200 proceeds to act 210. If the average of the probabilities calculated in act 206 does not exceed the threshold probability, this may indicate that the sequence of images does not depict the particular anatomical view and calculation of the quality of the sequence should not proceed, and the process 200 proceeds to act 216.

In act 210, the computing device calculates a quality of the ultrasound image. Further description of calculating the quality of an ultrasound image may be found with reference to process 100. The process 200 proceeds from act 210 to act 212.

In act 212, the computing device averages the quality of the image with the qualities of other images in a sequence (calculated in accordance with acts 102-110) to produce the quality of the sequence of images. In some embodiments, the computing device may use an arithmetic mean. The process 200 proceeds from act 212 to act 214.

In act 214, the computing device generates for display, during the imaging, an indicator of the live quality of the sequence of images. In some embodiments, the indicator of the live quality of the sequence of images may be one or more of a color bar, a pie graph, or a number. For example, the indicator may include a bar-shaped frame and a slider that may be located at any position along the length of the bar. The distance of the slider from one end of the bar relative to the total length of the bar may be proportional to the quality. The bar may have varying colors along its length, in particular reddish colors in regions near the first end of the bar, yellowish colors in regions near the middle of the bar, and greenish colors in regions near the second end of the bar. When the slider is located on a more reddish color, the quality may be lower, and when the slider is located on a more greenish color, the quality may be higher.

As another example, the indicator may include a bar-shaped frame having a first end and a second end, and a color bar within the frame may extend from the first end towards the second end. The length of the color bar relative to the length of the frame may be proportional to the quality of the sequence of images. For example, if the color bar extends halfway from the first end to the second end of the frame, the quality may be 50% on a scale of 0% to 100%. The color bar may be any shape, and may be straight or curved. The color bar may have varying colors along its length, for example reddish colors in regions near the first end of the frame, yellowish colors in regions near the middle of the frame, and greenish colors in regions near the second end of the frame. In embodiments in which the bar is colored, if a first sequence of images has a higher quality than a second sequence of images, an indicator of the quality of the first sequence of images may have a color bar extending farther from the first end to the second end of the frame than an indicator of the quality of the second sequence of images. Furthermore, the color bar for the first sequence of images may contain more greenish colors than the color bar for the second sequence of images. In some embodiments, the bar within the frame may not be colored.

In some embodiments, the computing device may also generate for display an acceptability indicator that indicates whether the live quality of the sequence of images collected exceeds a threshold quality. The threshold quality may be a quality beyond which an ultrasound images or sequence of ultrasound images is suitable for a particular automatic measurement. In some embodiments, the acceptability indicator may appear only when the live quality of the sequence of images collected exceeds a threshold quality. For example, the acceptability indicator may be a checkmark that appears when the live quality of the sequence of images collected exceeds a threshold quality. In embodiments in which the length of a color bar within a frame relative to the total length of the frame indicates quality, the acceptability indicator may be a marking on the frame of the color bar at a certain distance from one end of the frame, such that the distance from the end of the frame to the location of the acceptability indicator is proportional to the threshold quality. When the color bar within the frame extends beyond the acceptability indicator, this may be an indication that the live quality of the sequence of images collected is acceptable for performing a particular automatic measurement. In embodiments in which the distance of a slider from one end of a bar relative to the total length of the bar indicates quality, the acceptability indicator may be a marking on the frame of the color bar at a certain distance from one end of the frame, such that the distance from the end of the frame to the location of the acceptability indicator is proportional to the threshold quality. When the slider is positioned beyond the acceptability indicator, this may be an indication that the live quality of the sequence of images collected is acceptable for performing a particular automatic measurement. Further description of the live quality indicator and the acceptability indicator may be found with reference to FIGS. 6-21.

In some embodiments, the computing device may generate for display the live quality indicator simultaneously with instructions for positioning the ultrasound device (e.g., "MOVE UP," "MOVE LEFT," "MOVE RIGHT," "ROTATE CLOCKWISE," "ROTATE COUNTER-CLOCKWISE," or "MOVE DOWN"). In such embodiments, the operator may initially follow the instructions for positioning the ultrasound device, and once the operator has moved the ultrasound device to a region where there are no further repositioning instructions, the operator may use the quality indicator and the "hill climbing" procedure discussed above to further reposition the ultrasound device near the region. Accordingly, the instructions for positioning the ultrasound device may constitute fine positioning guidance and the quality indicator may constitute very fine positioning guidance. In some embodiments, the computing device may generate for display instructions for positioning the ultrasound device before generating for display the quality indicator, and generating for display the quality indicator once the operator has moved the ultrasound device to a region where there are no further repositioning instructions. For further description of generating instructions for moving an ultrasound device, see U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1.

Act 216 proceeds if the average of the probabilities calculated in act 206 does not exceed the threshold probability, which may indicate that the sequence of images does not depict the particular anatomical view and calculation of the quality of the sequence should not proceed. In act 216, the computing device generates for display, during the imaging an indicator that the quality of the sequence of ultrasound images has not been calculated. For example, the computing device may gray out the live quality indicator, not display the live quality indicator, or display some other text or symbol. In some embodiments, the computing device may generate for display an indicator that the operator should collect another sequence of images that depict the particular anatomical view.

In some embodiments, the computing device may calculate the live quality of a sequence of images (as described with reference to acts 204-212), generate for display an indicator of the live quality of the sequence of images (as described with reference to act 214), receive a new image that has been collected by the ultrasound device (as described with reference to act 202), remove the oldest image in the sequence of images (i.e., the image in the sequence of images that was collected longest ago), add the new image to the sequence of images, calculate the live quality of this new sequence of images (as described with reference to acts 204-212), and generate for display a new indicator of the live quality of the new sequence of images (as described with reference to act 214) to replace the indicator of the live quality of the previous sequence of images. Therefore, as more images are collected, the quality indicator may be updated in real-time.

In some embodiments, certain acts of the process 200 may be absent. For example, in some embodiments, acts 202-212 may be absent. In some embodiments, act 214 may be absent. In some embodiments, acts 204-208 and 216 may be absent. In some embodiments, other combinations of the acts of the process 200 may be absent. In some embodiments, the quality of the sequence of ultrasound images depicted in act 214 may be the same as the average of the probabilities calculated in act 206. In other words, acts 208-212 and 216 may be absent, and the computing device may display, at act 214, the average of the probabilities calculated in act 206. While the processes 200 has described calculating and displaying an indicator of the live quality of a sequence of ultrasound images, in some embodiments the computing device may calculate and display the live quality for a single ultrasound image. In such embodiments, no averaging may occur; the displayed quality may simply be the quality of the single ultrasound image. In other words, acts 206 and 212 may be absent. In some embodiments, other combinations of the acts of the process 200 may be absent.

FIG. 3 illustrates an example process 300 for performing an automatic measurement (e.g., calculation of ejection fraction) on a sequence of ultrasound images based on calculating the offline quality of the sequence of ultrasound images, in accordance with certain embodiments described herein. The offline quality may be a quality calculated after the sequence of ultrasound images has been saved to memory. The process 300 begins with act 302. In act 302, the computing device receives a selection to perform an automatic measurement. In some embodiments, the operator may select an option displayed on the display screen of the computing device to perform the automatic measurement. In some embodiments, the operator may select an option to record a sequence of ultrasound images, and after recording the sequence of ultrasound images, the computing device may automatically proceed with performing the automatic measurement. The process 300 proceeds from act 302 to act 304.

In act 304, the computing device receives a sequence of images. The sequence of images may have been saved to memory, for example, based on the operator selecting an option to record a sequence of ultrasound images. The memory may be, for example, on the computing device or a server in communication with the computing device. The process 300 proceeds from act 304 to act 306.

In act 306, the computing device calculates the offline quality of the sequence of images. In some embodiments, calculating the offline quality may include calculating a quality of each of the images in the sequence (as discussed above with reference to process 100) and selecting the offline quality as the image quality at a specific quantile ($5^{th}$ percentile, $10^{th}$ percentile, $15^{th}$ percentile, $20^{th}$ percentile, $25^{th}$ percentile, $30^{th}$ percentile, $35^{th}$ percentile, $40^{th}$ percentile, or any suitable percentile) of the image qualities of all the images in the sequence. In some embodiments, the specific percentile used may depend on the type of images in the sequence. For example, in some embodiments a higher percentile may be used for apical four chamber views of the heart vs. parasternal long axis views of the heart (e.g., 15th percentile for apical four chamber views of the heart and $25^{th}$ percentile for parasternal long axis views of the heart) while in other embodiments a higher percentile may be used for parasternal long axis views of the heart vs. apical four chamber views of the heart.

In some embodiments in which act 310 includes automatically measuring ejection fraction based on images of the heart, the procedure discussed above for calculating the offline quality may include additional features. In particular, in such embodiments, the computing device may select a portion of the sequence of images showing a full heart cycle and calculate the following:

1. The minimum image quality in a window of images near the image identified as end-diastole. The window of images may include the image identified as end-diastole and images that are temporally adjacent to end-diastole, such as a certain number of images (e.g., one, two, three, four, five, or any suitable number) before the image identified as end-diastole, and a certain number of images (e.g., one, two, three, four, five, or any suitable number) after the image identified as end-diastole.

2. The minimum image quality in a window of images near the image identified as end-systole. The window of images may include the image identified as end-systole and images that are temporally adjacent to end-systole, such as, a certain number of images (e.g., one, two, three, four, five, or any suitable number) before the image identified as end-systole, and a certain number of images (e.g., one, two, three, four, five, or any suitable number) after the image identified as end-systole.

3. The image quality at a specific quantile ($5^{th}$ percentile, $10^{th}$ percentile, $15^{th}$ percentile, $20^{th}$ percentile, $25^{th}$ percentile, or any suitable percentile) of the image qualities of all the images in the selected portion.

The minimum of the three qualities discussed above may be selected as the offline quality. This procedure effectively weighs images at and near end-systole and end-diastole higher than other images, which may be helpful because end-systole and end-diastole may be important events for calculating ejection fraction. The procedure may help to ensure that the offline quality is not high if images at and/or near end-systole or end-diastole are low quality, even if other images in the sequence are high quality. The process 300 proceeds from act 306 to act 308.

In act 308, the computing device determines whether the offline quality exceeds (or in some embodiments, exceeds or is equal to) a threshold quality (e.g., 50% on a scale of 0% to 100%). If the offline quality exceeds the threshold quality, the process 300 proceeds from act 308 to act 310. If the offline quality does not exceed the threshold quality, the process proceeds from act 308 to act 312.

Act 310 proceeds if the offline quality exceeds the threshold quality. In act 310, the computing device performs the automatic measurement on the sequence of ultrasound images. In some embodiments, the computing device may display the automatic measurement, and the computing device may also display the offline quality (e.g., as a number) of the sequence of ultrasound images on which the automatic measurement was performed.

Act 312 proceeds if the offline quality does not exceed the threshold quality. In act 310, the computing device displays an indication that the automatic measurement will not proceed. Additionally, the computing device may enter a manual mode in which the operator may perform manual measurements, which may involve manually annotating/segmenting image(s) and using those annotations/segmentations for measurements/calculations.

While the processes 300 has described calculating the offline quality of a sequence of ultrasound images, in some embodiments the computing device may calculate the offline quality for a single ultrasound image. In such embodiments, the quality that is compared to the threshold quality may simply be the quality of the single ultrasound image; no use of percentiles may be required.

In some embodiments, certain acts of the process 300 may be absent. For example, in some embodiments, act 302 may be absent. In some embodiments, acts 302-306 may be absent. In some embodiments, acts 306-312 may be absent. In some embodiments, other combinations of the acts of the process 300 may be absent.

While the above description has described the processes 100-300 as being performed by a computing device in operative communication with an ultrasound device, other devices, such as the ultrasound device itself or a server in communication with the computing device, may also perform these processes. Additionally, while the above description has described calculating qualities for ultrasound images, the same processes may also be used to calculate the qualities of other types of medical images, such as X-ray, computerized tomography (CT), and magnetic resonance imaging (MRI) images.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Figure 4:
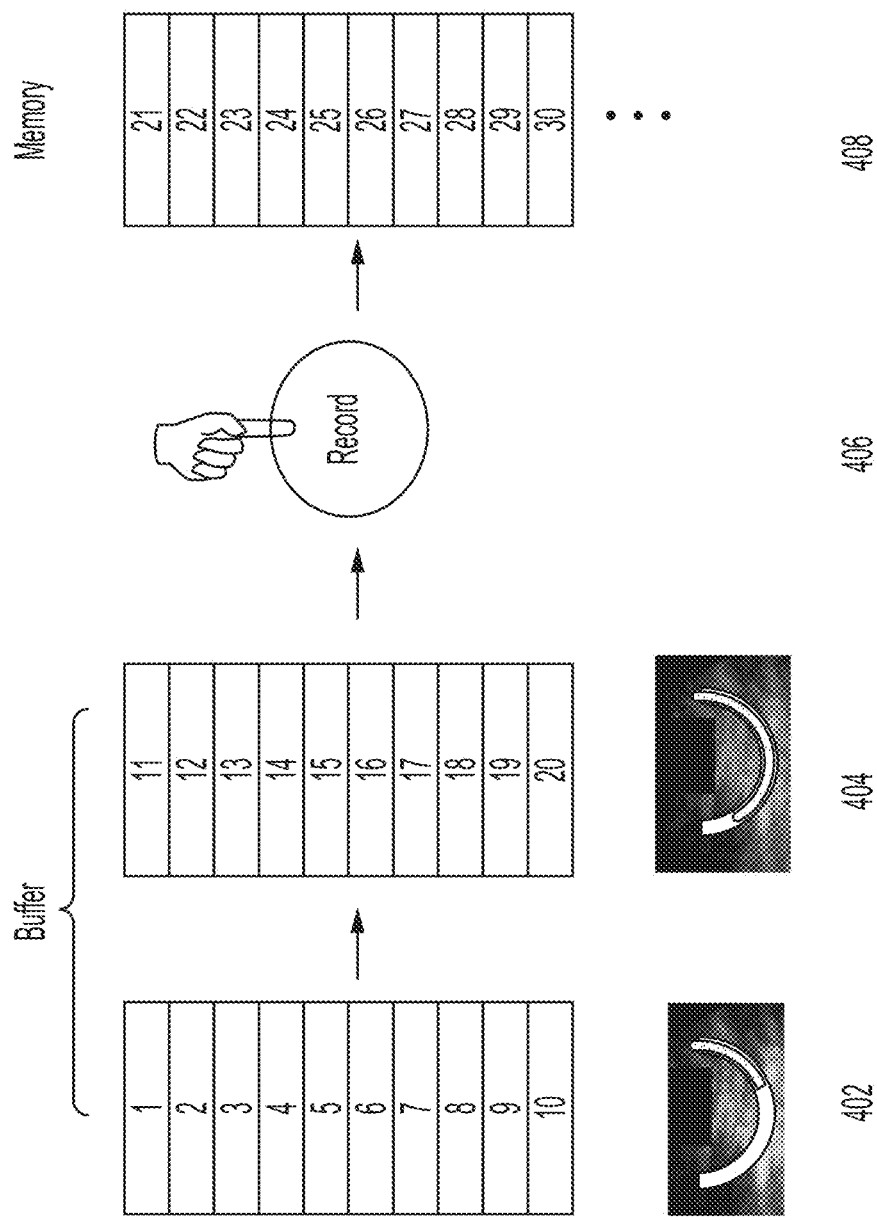
FIG. 4 shows a conceptual illustration of a process for saving images to memory for further use, in accordance with certain embodiments discussed herein.

FIG. 4 shows a conceptual illustration of a process for saving images to memory (e.g., non-volatile memory) for further use in accordance with certain embodiments discussed herein. For example, the images saved to memory may be used for automatically performing measurements (e.g., automatically calculating ejection fraction). In FIG. 4, consecutive images are represented as boxes with consecutively increasing numbers. In stage 402, the sequence of the ten previously collected images, images 1-10, are saved to a temporary storage buffer (e.g., volatile memory). The quality indicator indicates that the sequence of images 1-10 has a quality of approximately 40 on a scale of 0 to 100. In stage 404, after passage of time from stage 402, the next ten previously collected images, now images 11-20, are saved to the temporary storage buffer. The quality indicator indicates that the sequence of images 11-20 has a quality of approximately 80 on a scale of 0 to 100. In stage 406, the user presses a record button to initiate saving of images to memory (e.g., non-volatile memory). In stage 408, forthcoming collected images, namely images 21 and onwards, are saved to memory.

In some embodiments, the computing device may automatically save to memory (e.g., non-volatile memory) a sequence of images upon calculating that the live quality of the sequence of images exceeds a threshold quality. For example, the computing device continuously saving in a buffer (e.g., volatile memory) the previous N images collected during imaging. The computing device may further remove, when a new image is collected, the oldest image in the buffer (i.e., the image in the buffer that was collected longest ago) from the buffer, adding the new image to the buffer, and calculating the quality of the sequence of image currently in the buffer. The computing may further automatically save to memory the sequence of images to memory if the live quality of the sequence of images exceeds a threshold, or if the live quality of the sequence of images does not exceed a threshold, receive another image to replace the oldest image and repeating the above procedure for the new sequence of images in the buffer. In such embodiments, an operator may not need to trigger a record button or other means for triggering the saving of images to memory, as the computing device may automatically saving images to memory. Additionally, in this "lookback" feature, the same sequence of images for which live quality is calculated is saved to memory, rather than saving to memory a future sequence of images based on a previous sequence of images having a certain calculated live quality. This may be helpful if, for example, the future sequence of images collected at a certain location does not have as high a quality as the previous sequence of images collected at that location. This feature is illustrated in FIG. 5.

Figure 5:
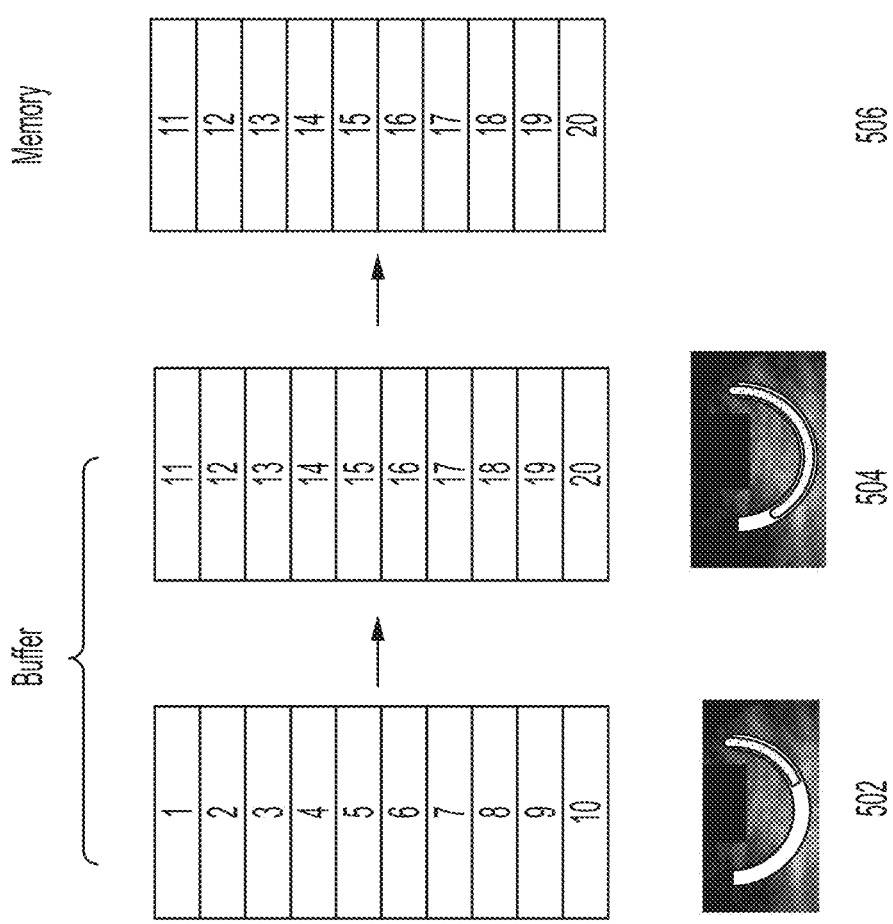
FIG. 5 shows a conceptual illustration of another process for saving images to memory for further use, in accordance with certain embodiments discussed herein.

FIG. 5 shows a conceptual illustration of another process for saving images to memory (e.g., non-volatile memory) for further use in accordance with certain embodiments discussed herein. In stage 502, the sequence of the ten previously collected images, images 1-10, are saved to a temporary storage buffer (e.g., volatile memory). The quality indicator indicates that the sequence of images 1-10 has a quality of approximately 40 on a scale of 0 to 100. In stage 504, after passage of time from stage 502, the ten previously collected images, now images 11-20, are saved to the buffer. The quality indicator indicates that the sequence of images 11-20 has a quality of approximately 80 on a scale of 0 to 100. In stage 506, it is determined that the quality of the sequence of images 11-20 currently stored in the buffer exceeds a threshold quality, and the sequence of images 11-20 are saved to memory from the buffer.

Figure 6:
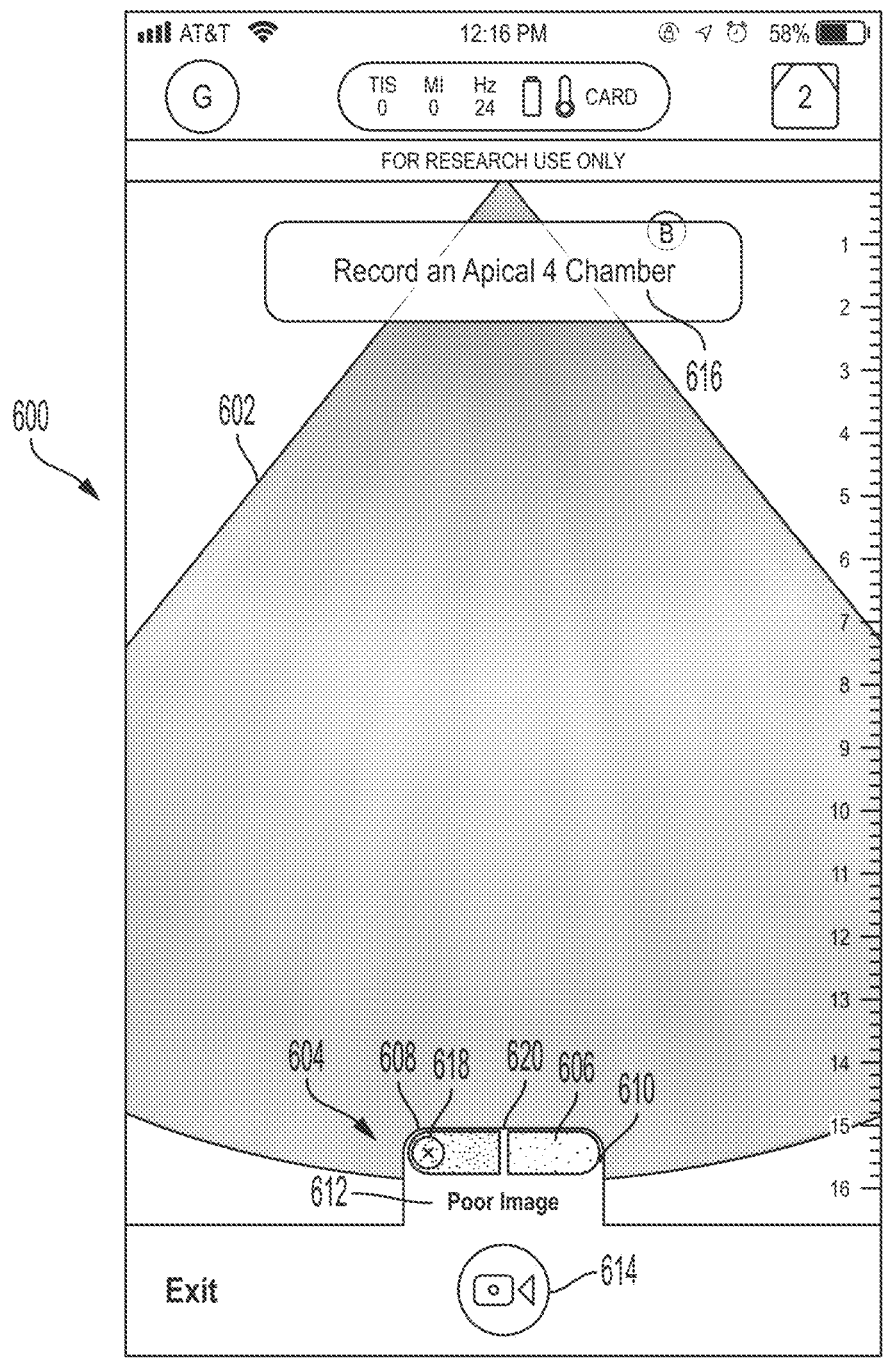
FIG. 6 illustrates an example of a graphical user interface (GUI) that may be displayed by a display screen of a computing device during imaging with an ultrasound device in communication with the computing device, in accordance with certain embodiments described herein.

FIG. 6 illustrates an example of a graphical user interface (GUI) 600 that may be displayed by a display screen of a computing device during imaging with an ultrasound device in communication with the computing device, in accordance with certain embodiments described herein. The GUI 600 displays an ultrasound image 602, a live quality indicator 604, a record option 614, and an instruction 616. The live quality indicator 604 includes a bar 606 having a first end 608 and a second end 610, a slider 618, an acceptability indicator 620, and text 612.

The ultrasound image 602 may be formed from ultrasound data currently being collected by the ultrasound device that is in communication with the computing device. In FIG. 6, the live quality indicator 604 is superimposed on the ultrasound image 602, while in other embodiments, the live quality indicator 608 may not be superimposed on the ultrasound image 602. The live quality indicator 604 indicates a quality calculated for a sequence of images previously collected with the ultrasound device, where the sequence of images constitutes a fixed number of images (e.g., the previous 10 images) or the sequence of images constitutes images collected over a fixed period of time (e.g., the previous 2 seconds). The quality calculated for the sequence of images describes the quality of the sequence of images for performing a particular automatic measurement (e.g., calculating a clinical metric such as ejection fraction). The slider 618 may be located at any position along the length of the bar, and the distance of the slider 618 from the first end 608 of the bar 606 relative to the total length of the bar 606 may be proportional to the quality. In FIG. 6, the slider 618 is located at the first end 608 of the bar 606, indicating that the live quality may be approximately 0% on a scale of 0% to 100%. The bar 606 has varying colors along its length, in particular reddish colors (shown with dense stippling) in regions near the first end 608 of the bar 606, yellowish colors (shown with medium stippling) in regions near the middle of the bar 606, and greenish colors (shown with light stippling) in regions near the second end 610 of the bar 606. When the slider is located on a more reddish color (shown with dense stippling), the quality may be lower, and when the slider is located on a more greenish color (shown with light stippling), the quality may be higher. Other shapes, sizes, and forms for the bar 606 may be possible.

In FIG. 6, the acceptability indicator 620 is a black bar located approximately 50% of the distance from the first end 608 to the second end 610 of the bar 606. The acceptability indicator 620 indicates a threshold quality above which a sequence of images may be considered acceptable or not acceptable for performing the particular automatic measurement. Thus, a quality below 50% on a scale of 0% to 100% may indicate that the sequence of images is considered unacceptable for performing the particular automatic measurement while a quality above 50% may indicate that the sequence of images is considered acceptable for performing the particular automatic measurement. In FIG. 6, the quality shown is approximately 0%, and thus the sequence of images may be considered unacceptable for performing the particular automatic measurement. In FIG. 6, because the quality is below the threshold indicated by the acceptability indicator, the slider 618 includes an "x" symbol that further indicates that the sequence of images is considered not acceptable for performing the particular automatic measurement. The live quality indicator 604 further includes text 612 indicating whether the sequence of images is considered acceptable for performing the particular automatic measurement. In FIG. 6, because the quality is below the threshold indicated by the acceptability indicator, the text 612 reads "Poor Image."

The GUI 600 further shows a record button 614 which, upon being selected, trigger saving of images being collected to a memory (e.g., non-volatile memory) of the computing device. The GUI 600 further shows an instruction 616 for collecting an ultrasound image of a particular anatomical view (in the example of FIG. 6, an apical four-chamber view of the heart) to be used for performing the particular automatic measurement (e.g., calculating ejection fraction).

Figure 7:
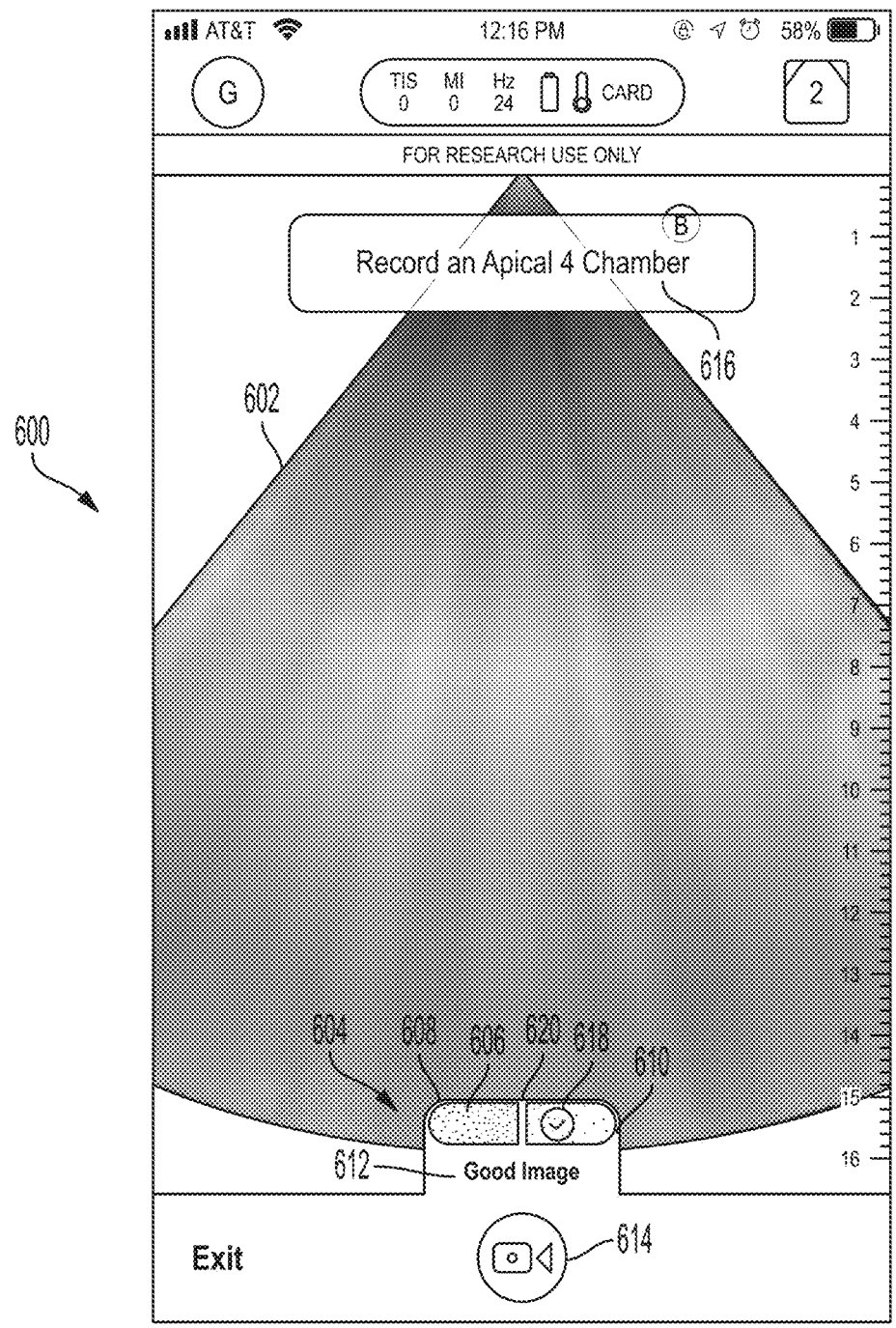
FIG. 7 illustrates another example of the GUI of FIG. 6, in accordance with certain embodiments described herein.

FIG. 7 illustrates an example of the GUI 600, where the live quality indicator 604 indicates a different quality than in FIG. 6, in accordance with certain embodiments described herein. FIG. 7 differs from FIG. 6 in that in FIG. 7, the slider 618 is located approximately 60% of the distance from the first end 608 to the second end 610 of the bar 606, indicating that the live quality may be approximately 60% on a scale of 0% to 100%. Because the quality is above the threshold indicated by the acceptability indicator, the slider 618 includes a checkmark symbol that further indicates that the sequence of images is considered acceptable for performing the particular automatic measurement, and the text 612 reads "Good Image."

Figure 8:
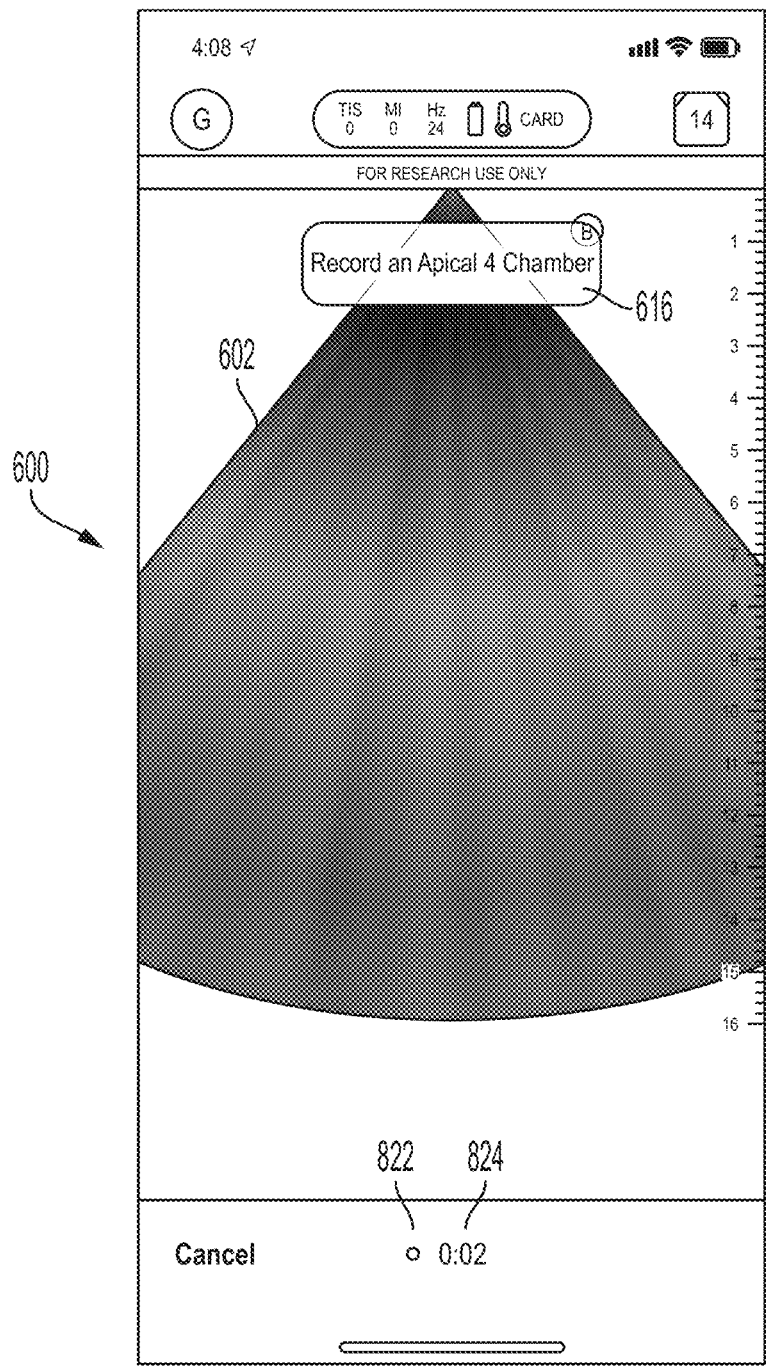
FIG. 8 illustrates another example of the GUI of FIG. 6, in accordance with certain embodiments described herein.

Upon selection of the record option 614, ultrasound images may be saved to memory as they are collected. Ultrasound images may be saved for a particular period of time. FIG. 8 illustrates an example of the GUI 600 after selection of the record option 614, in accordance with certain embodiments described herein. In FIG. 8, the GUI 600 displays a record symbol 822 (a red circle) and a record time indicator 824. The record symbol 822 may be any symbol indicates that recording of ultrasound images to memory is taking place. The record time indicator 824 indicates the amount of time left in the current recording process. In FIG. 8, the record time indicator 824 indicates that there are two more seconds of recording to take place. In some embodiments, instead of the record time indicator 824 indicating the amount of time left in the current recording process, the record time indicator 824 may indicate how much time has elapsed in the current recording process.

Figure 9:
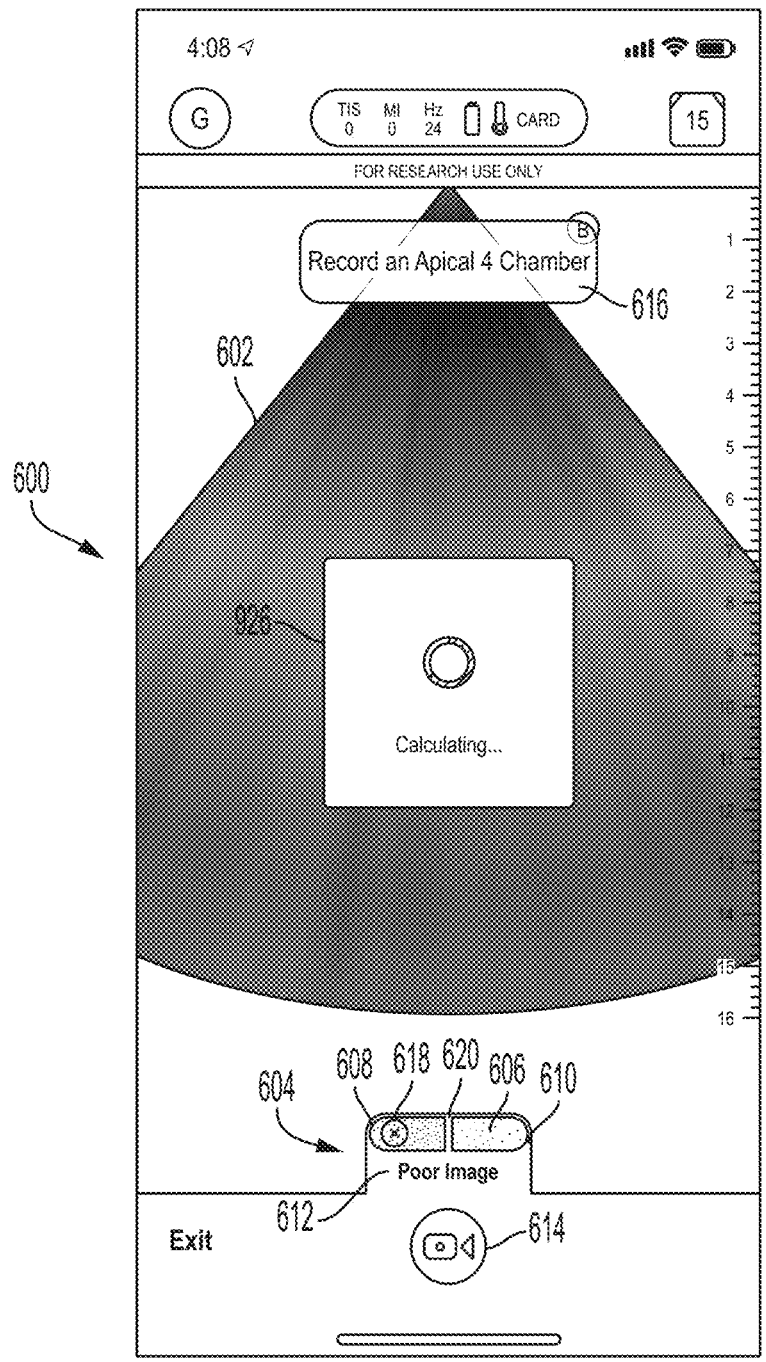
FIG. 9 illustrates another example of the GUI of FIG. 6, in accordance with certain embodiments described herein.

FIG. 9 illustrates an example of the GUI 600 after recording of ultrasound images to memory, in accordance with certain embodiments described herein. The GUI 600 includes an indicator 926 that the computing device is in the process of performing a calculation (e.g., calculating ejection fraction) based on the recorded ultrasound images.

Figure 10:
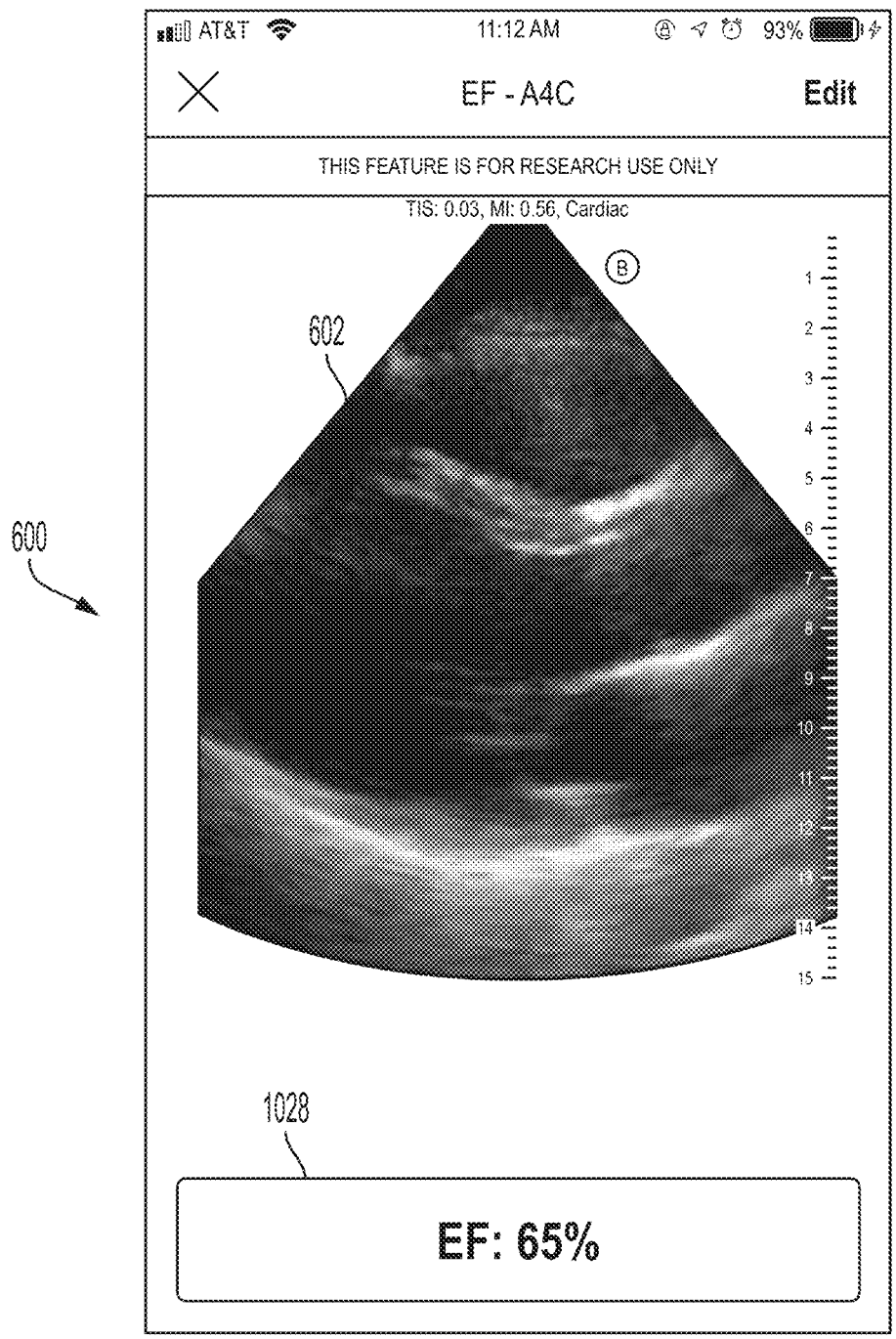
FIG. 10 illustrates another example of the GUI of FIG. 6, in accordance with certain embodiments described herein.

FIG. 10 shows an example of the GUI 600 after a calculation based on recorded ultrasound images, in accordance with certain embodiments described herein. The GUI 600 includes a result 1028 of the calculation (in FIG. 10, an ejection fraction value, 65%).

Figure 11:
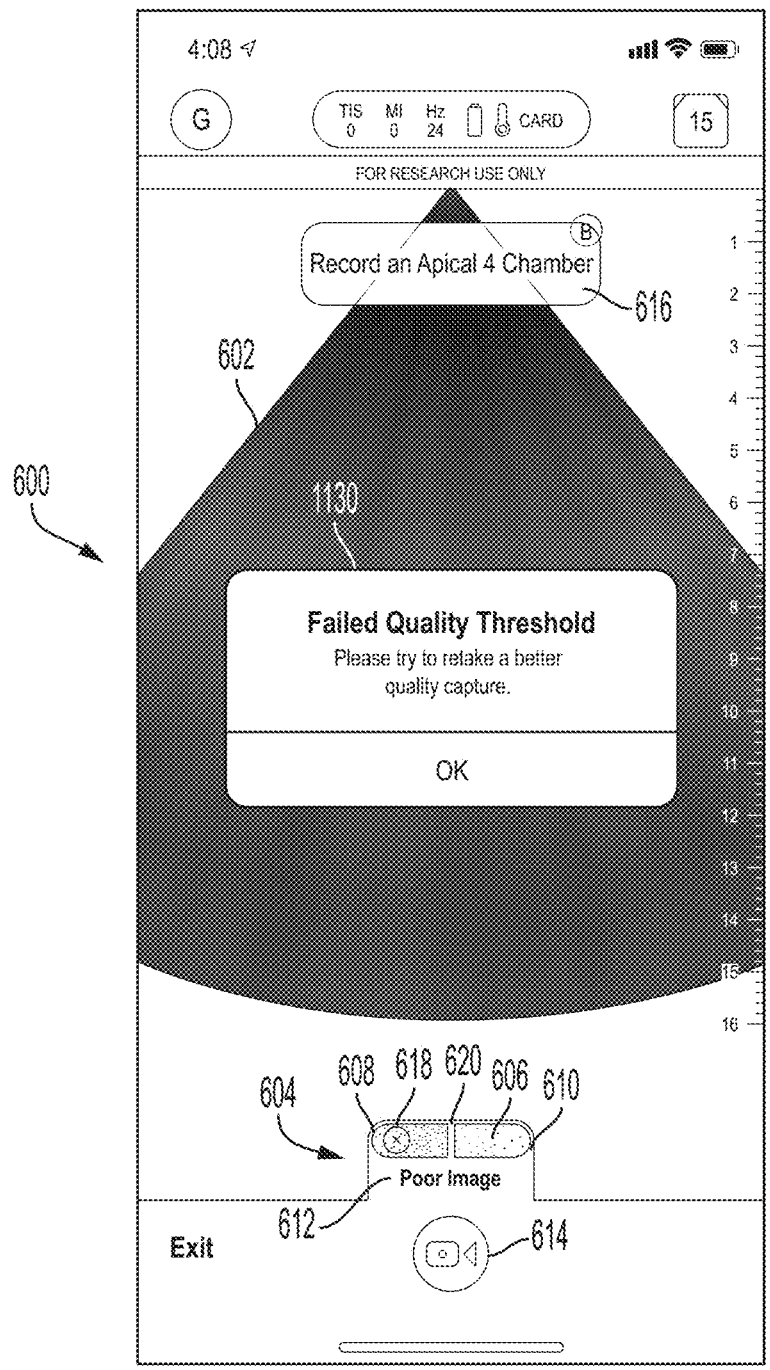
FIG. 11 illustrates another example of the GUI of FIG. 6, in accordance with certain embodiments described herein.

FIG. 11 shows another example of the GUI 600 after recording of ultrasound images to memory, in accordance with certain embodiments described herein. As discussed above, in some embodiments automatic calculation may not proceed if an offline quality calculated for recorded ultrasound images does not exceed a threshold quality. In FIG. 11, because the offline quality calculated for the recorded ultrasound images does not exceed a threshold quality, the GUI 600 includes an indicator 1130 indicating that the quality of the recorded ultrasound images is too low to perform the automatic measurement, and requesting that the operator record another sequence of images for performing the automatic measurement.

Figure 12:
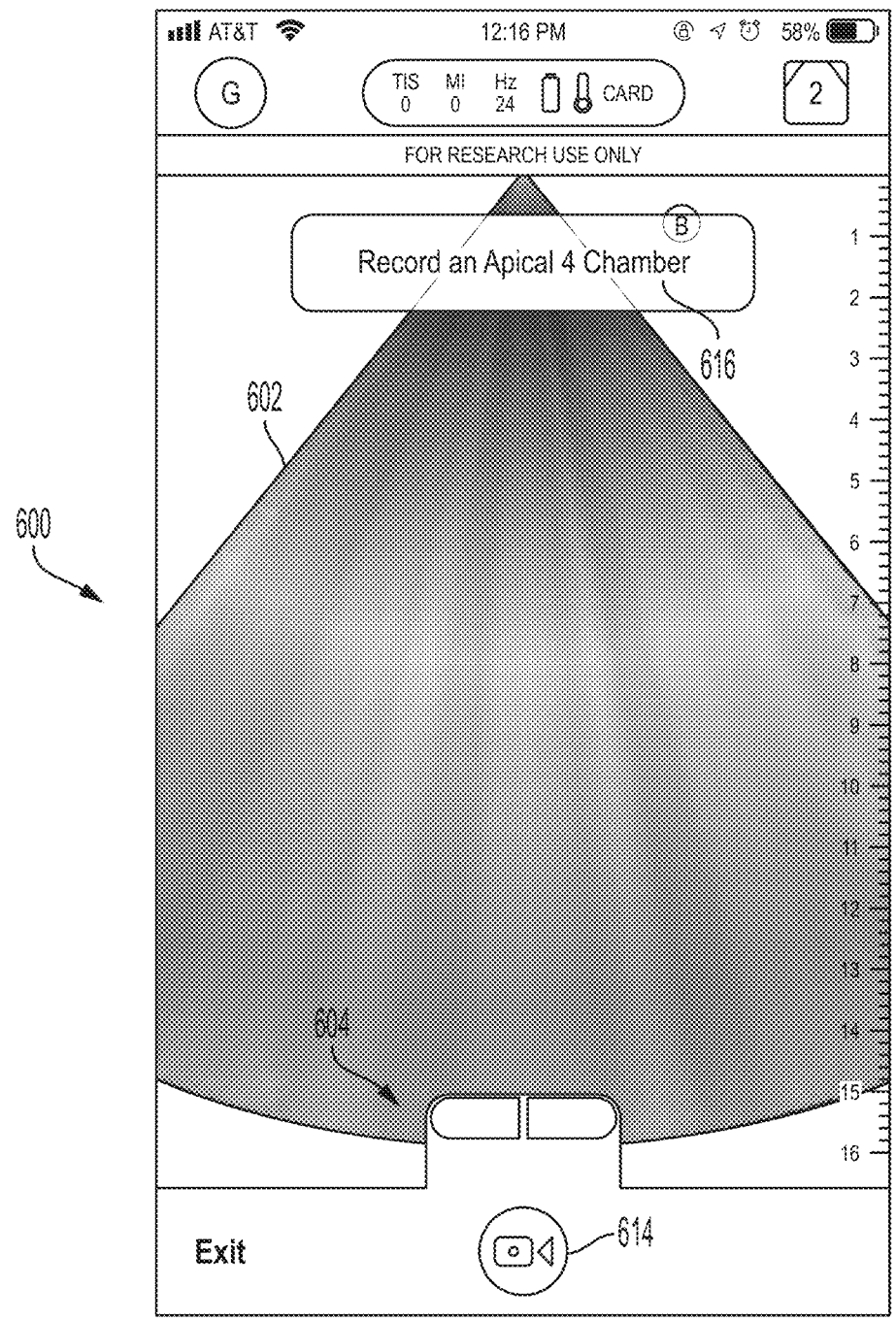
FIG. 12 illustrates another example of the GUI of FIG. 6, in accordance with certain embodiments described herein.

FIG. 12 illustrates another example of the graphical user interface (GUI) 600, in accordance with certain embodiments described herein. As discussed above, in some embodiments a quality calculated for an ultrasound image may not be meaningful if the ultrasound image does not depict a particular anatomical view for which the quality metric is designed. In FIG. 12, because the ultrasound image does not depict a particular anatomical view (e.g., an apical four-chamber view of the heart), the live quality indicator 604 does not show a quality calculated or the collected ultrasound image 602. Instead, the live quality indicator 604 is grayed out. In some embodiments, the live quality indicator 604 may take other forms to indicate that the quality has not been calculated for the collected ultrasound image 602. In some embodiments, the live quality indicator 604 is not shown when the ultrasound image does not depict a particular anatomical view.

Figure 13:
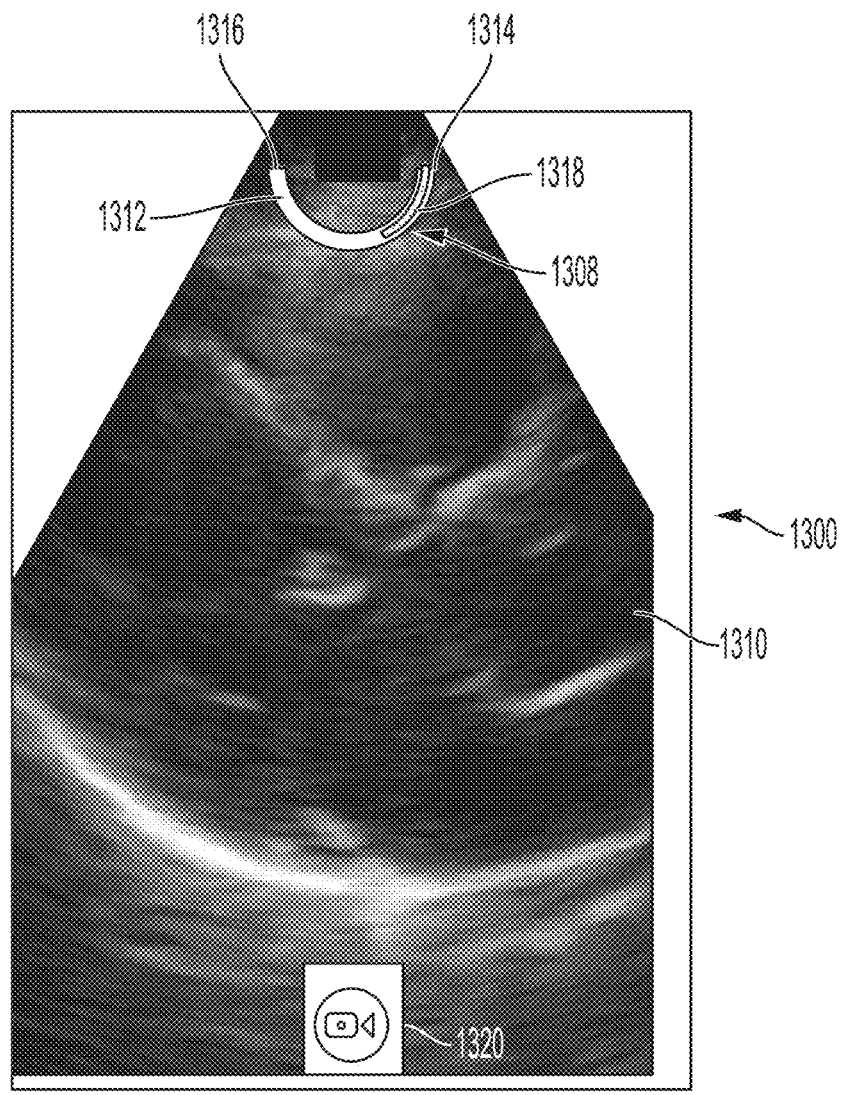
FIG. 13 illustrates an example of another GUI that may be displayed by a display screen of a computing device during imaging with an ultrasound device in communication with the computing device, in accordance with certain embodiments described herein.

FIG. 13 illustrates an example of another graphical user interface (GUI) 1300 that may be displayed by a display screen of a computing device during imaging with an ultrasound device in communication with the computing device, in accordance with certain embodiments described herein. The GUI 1300 displays a live quality indicator 1308 superimposed on an ultrasound image 1310. The ultrasound image 1310 may be formed from ultrasound data currently being collected by an ultrasound device that is in communication with the computing device 1304. In some embodiments, the live quality indicator 1308 may not be superimposed on an ultrasound image. The live quality indicator 1308 includes a frame 1312 having a first end 1314 and a second end 1316. The live quality indicator 1308 further includes a bar 1318 extending from the first end 1314 towards the second end 1316. The length of the bar 1318 relative to the length of the frame 1312 from the first end 1314 to the second end 1316 is proportional to the quality of a sequence of images collected with the ultrasound device. In FIG. 13, the bar 1318 extends approximately 40% of the distance between the first end 1314 and the second end 1316, indicating that the live quality may be approximately 40% on a scale of 0% to 100%. The live quality may be calculated for a sequence of images previously collected during imaging, where the sequence of images constitutes a fixed number of images (e.g., the previous 10 images) or the sequence of images constitutes images collected over a fixed period of time (e.g., the previous 2 seconds). The bar 1318 has varying colors along its length, in particular reddish colors (shown with dense stippling) in regions near the first end 1314 of the frame 1312 and yellowish colors (shown with medium stippling) in regions near the middle of the frame 1312. While the bar 1318 is shown as rectangular and curved, this is not limiting, and the bar 1318 may be straight and/or any other shape. In some embodiments, the live quality indicator 1308 may be a pie graph or a number. The GUI 1300 further shows a record button 1320 which, upon being selected, triggers saving of images being collected to a memory (e.g., non-volatile memory) of the computing device.

Figure 14:
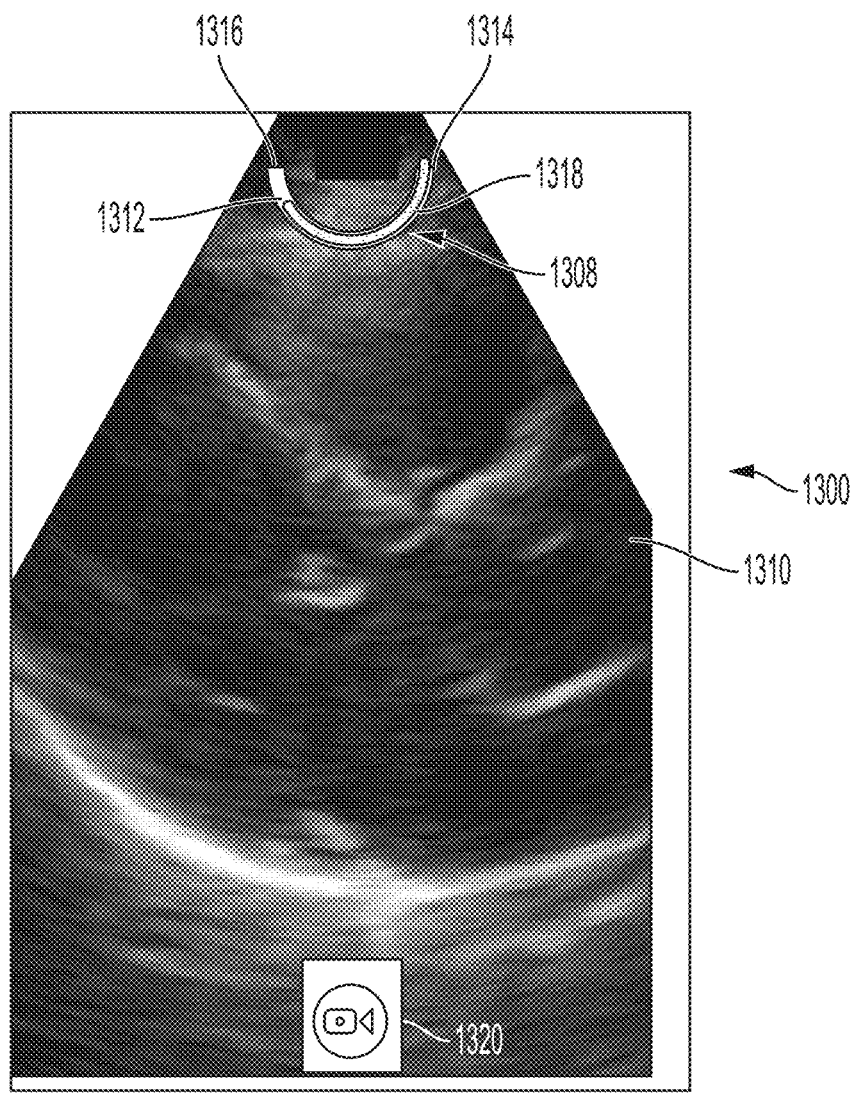
FIG. 14 illustrates another example of the GUI of FIG. 13, in accordance with certain embodiments described herein.

FIG. 14 shows another example of the GUI 1300 where the live quality indicator 1308 indicates a different quality than in FIG. 13, in accordance with certain embodiments described herein. In FIG. 14, the bar 1318 extends approximately 80% of the distance between the first end 1314 and the second end 1316, indicating that the live quality may be approximately 80% on a scale of 0% to 100%. The bar 1318 has varying colors along its length, in particular reddish colors (shown with dense stippling) in regions near the first end 1314 of the frame 1312, yellowish colors (shown with medium stippling) in regions near the middle of the frame 1312, and greenish colors (shown with light stippling) in regions near the second end 1316 of the frame 1312. Accordingly, the bar 1318 in FIG. 14 includes more greenish colors (shown with light stippling) than the bar 1318 in FIG. 13.

Figure 15:
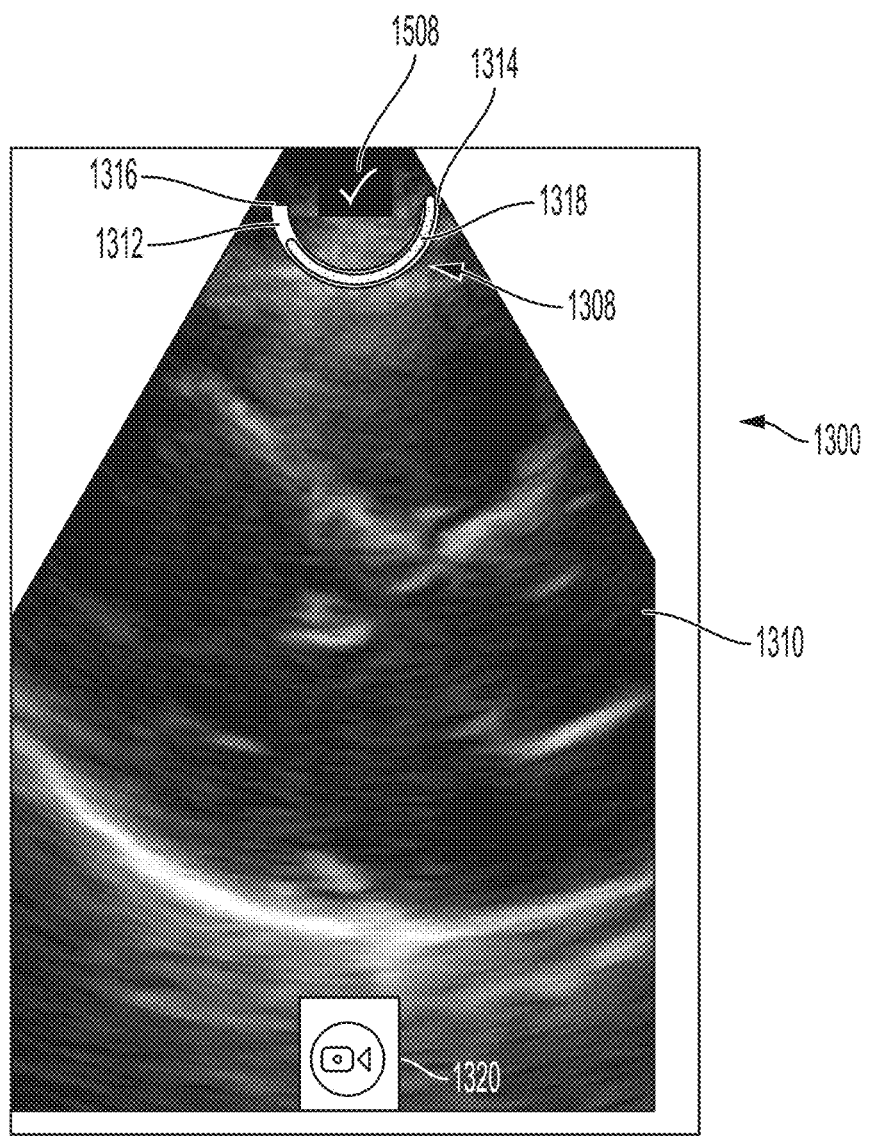
FIG. 15 illustrates another example of the GUI of FIG. 13, in accordance with certain embodiments described herein.

FIG. 15 shows another example of the GUI 1300 including an acceptability indicator 1508, in accordance with certain embodiments described herein. The acceptability indicator 1508 may appear when the calculated live quality of a sequence of images collected exceeds a threshold quality and may indicate that the sequence of images is of acceptable quality for use in performing a particular automatic measurement (e.g., automatic measurement of ejection fraction). In FIG. 15, the bar 1318 extends approximately 80% of the distance between the first end 1314 and the second end 1316, indicating that the live quality may be approximately 80% on a scale of 0% to 100%. The threshold quality may be, for example, 70%, and therefore the acceptability indicator 1508 is generated for display. In FIG. 15, the acceptability indicator 1508 is a checkmark, but any indicator of acceptability, such as the word "OK," may be used.

Figure 16:
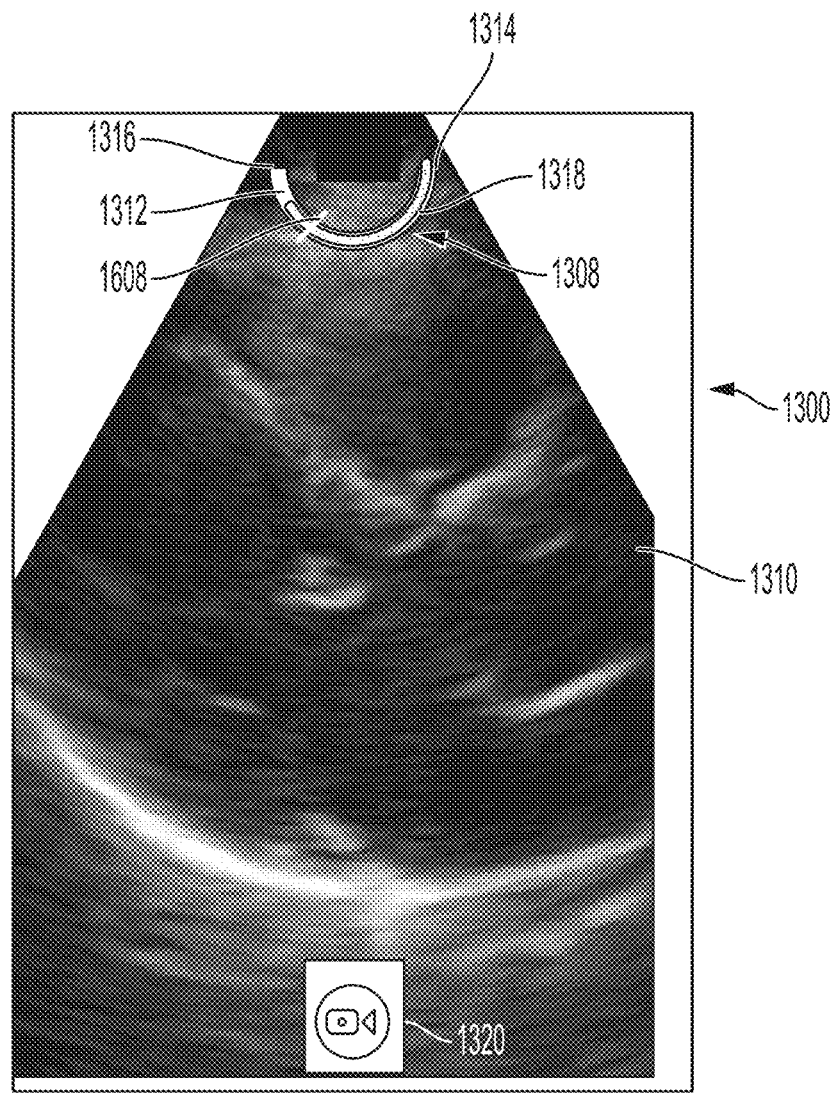
FIG. 16 illustrates another example of the GUI of FIG. 13, in accordance with certain embodiments described herein.

FIG. 16 shows another example of the GUI 1300 including an acceptability indicator 1608, in accordance with certain embodiments described herein. The acceptability indicator 1608 is a line located at a certain location between the first end 1314 and the second end 1316 of the frame 1312. The distance from the first end 1314 of the frame 1312 to the location of the acceptability indicator 1608 is proportional to the threshold quality. In FIG. 16, the acceptability indicator is located approximately 70% of the distance between the first end 1314 and the second end 1316 of the frame 1312, indicating that the threshold quality may be approximately 70% on a scale of 0% to 100%. Extension of the bar 1318 beyond the acceptability indicator 1608, as shown in FIG. 16, may indicate that the live quality of the sequence of images exceeds the threshold quality and therefore may indicate that the sequence of images is of acceptable quality for use in performing an automatic measurement (e.g., automatic measurement of ejection fraction).

Figure 17:
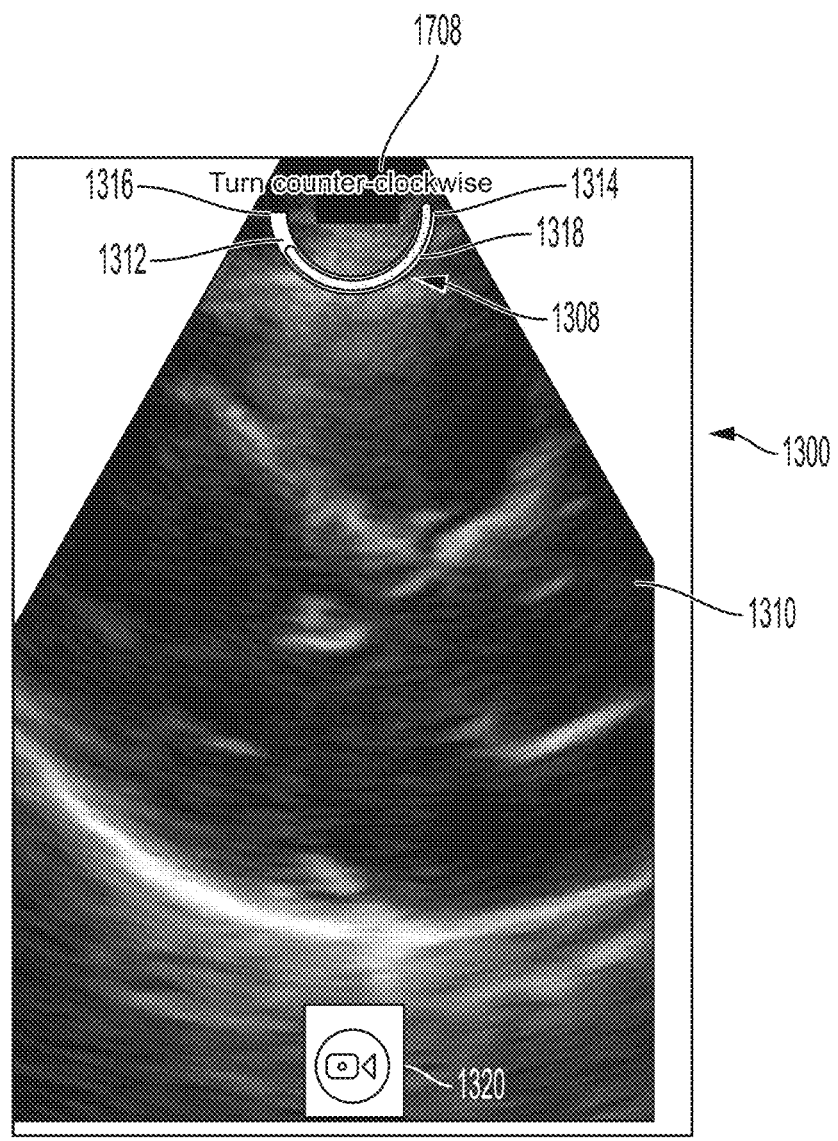
FIG. 17 illustrates another example of the GUI of FIG. 13, in accordance with certain embodiments described herein.

FIG. 17 shows another example of the GUI 1300 including an instruction 1708 for positioning an ultrasound device in order to collect an ultrasound image depicting a particular anatomical view, in accordance with certain embodiments described herein.

Figure 18:
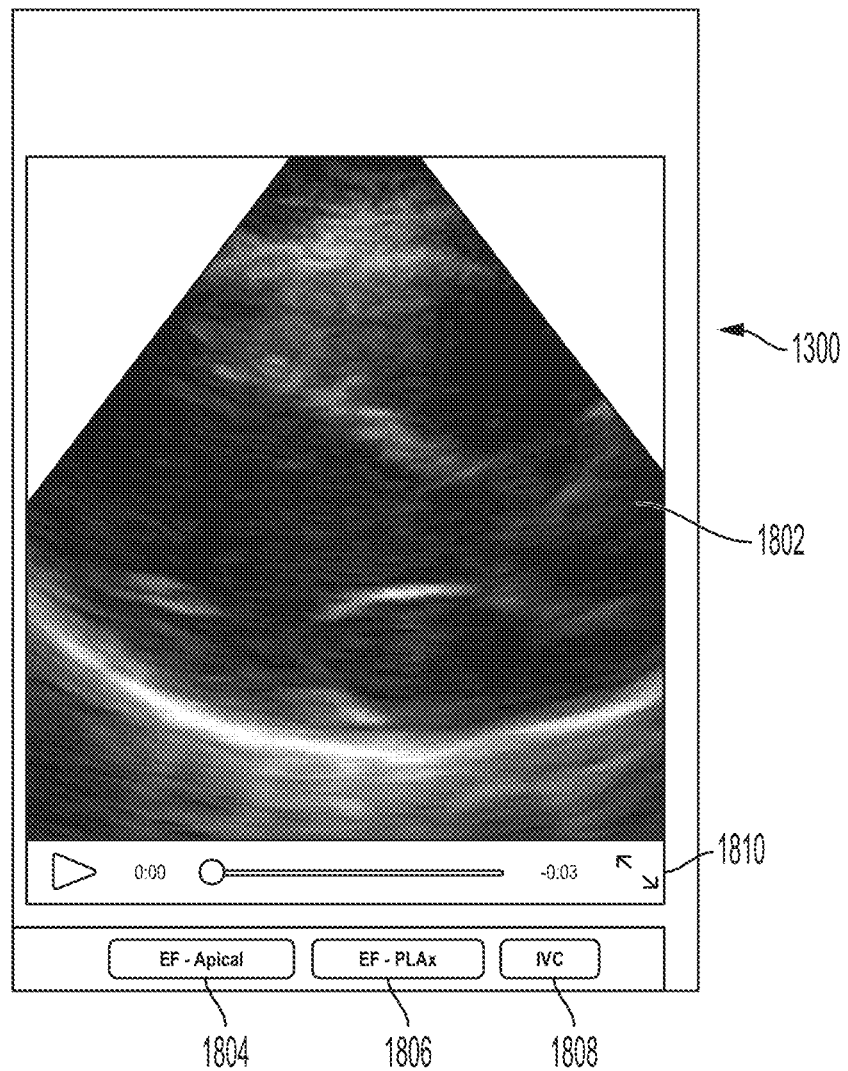
FIG. 18 illustrates another example of the GUI of FIG. 13, in accordance with certain embodiments described herein.

FIG. 18 shows another example of the GUI 1300, in accordance with certain embodiments described herein. In FIG. 18, the GUI 1300 includes a video 1802 of a sequence of ultrasound images, a measurement option 1804, a measurement option 1806, a measurement option 1808, and a video control bar 1810. The video 1802 may play through a collected sequence of ultrasound images, one image after another, in chronological order of collection. The video control bar 1810 may allow a user to play/pause the video 1802, skip to various locations within the video 1802, and maximize the area of the video 1802 within the display screen 1300. The video control bar 1810 also shows the time within the video 1802 of the image currently being shown on the GUI 1300 and the time remaining in the video 1802. Selection of the measurement option 1804 may trigger automatic measurement of ejection fraction in the collected sequence of images for images collected in the apical four chamber view. Selection of the measurement option 1806 may trigger automatic measurement of ejection fraction in the collected sequence of images for images collected in the parasternal long axis view. Selection of the measurement option 1808 may trigger automatic measurement of the collapsibility of the inferior vena cava (IVC), which may include the following steps: (1) Perform a segmentation on each image in the sequence of images to identify the IVC in the image, (2) Identify two points in each image representing endpoints of the diameter of the IVC, (3) Find the maximum diameter (i.e., the maximum distance between the identified endpoints) and the minimum diameter (i.e., the minimum distance between the identified endpoints) among the images in the sequence, (4) Use the following formula to calculate IVC collapsibility: IVC collapsibility=(max diameter−min diameter)/(mean diameter)×100. IVC collapsibility may be a metric for congestive heart failure.

Figure 19:
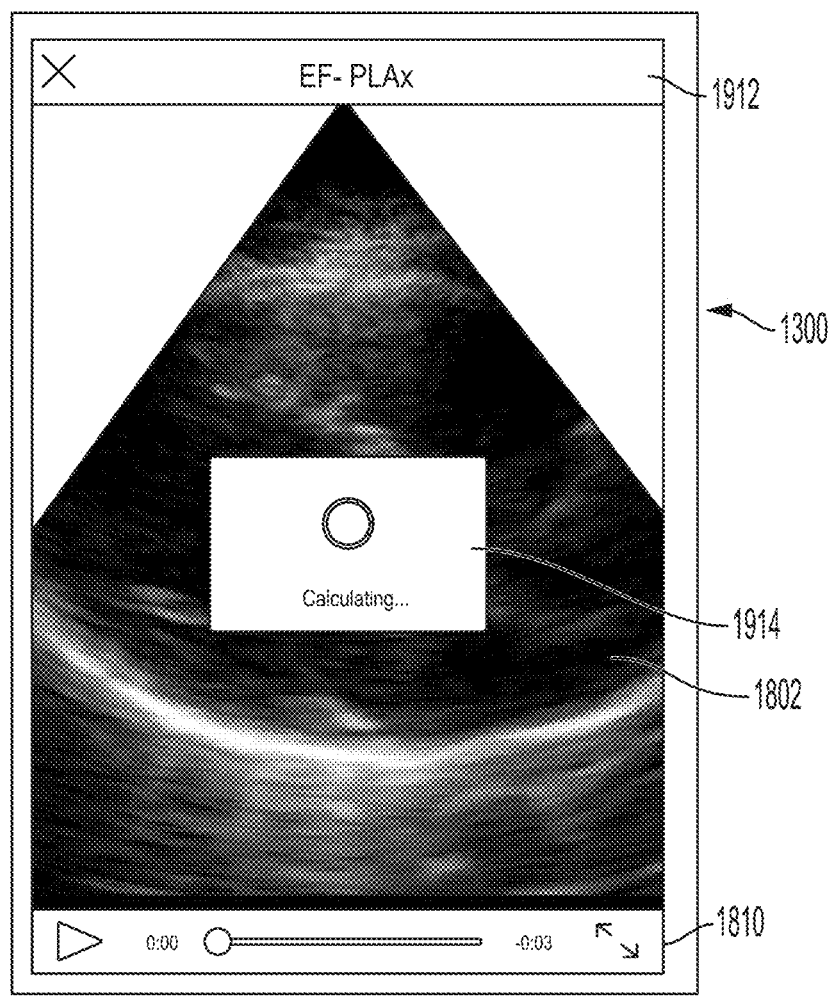
FIG. 19 illustrates another example of the GUI of FIG. 13, in accordance with certain embodiments described herein.

FIG. 19 shows another example of the GUI 1300 during an automatic measurement on a sequence of images, for example after selection of one of the measurement options 1804, 1806, or 1808 from the user interface 1800 of FIG. 18, in accordance with certain embodiments described herein. In FIG. 19, the GUI 1300 includes an indicator 1912 of the type of automatic measurement being performed (in the example of FIG. 19, measurement of ejection fraction in a sequence of images collected in the parasternal long axis view). The GUI 1300 also includes an indicator 1914 that the computing device is in the process of calculating the automatic measurement. As discussed above, automatic measurement may only proceed if an offline quality calculated for the sequence of images exceeds a threshold.

Figure 20:
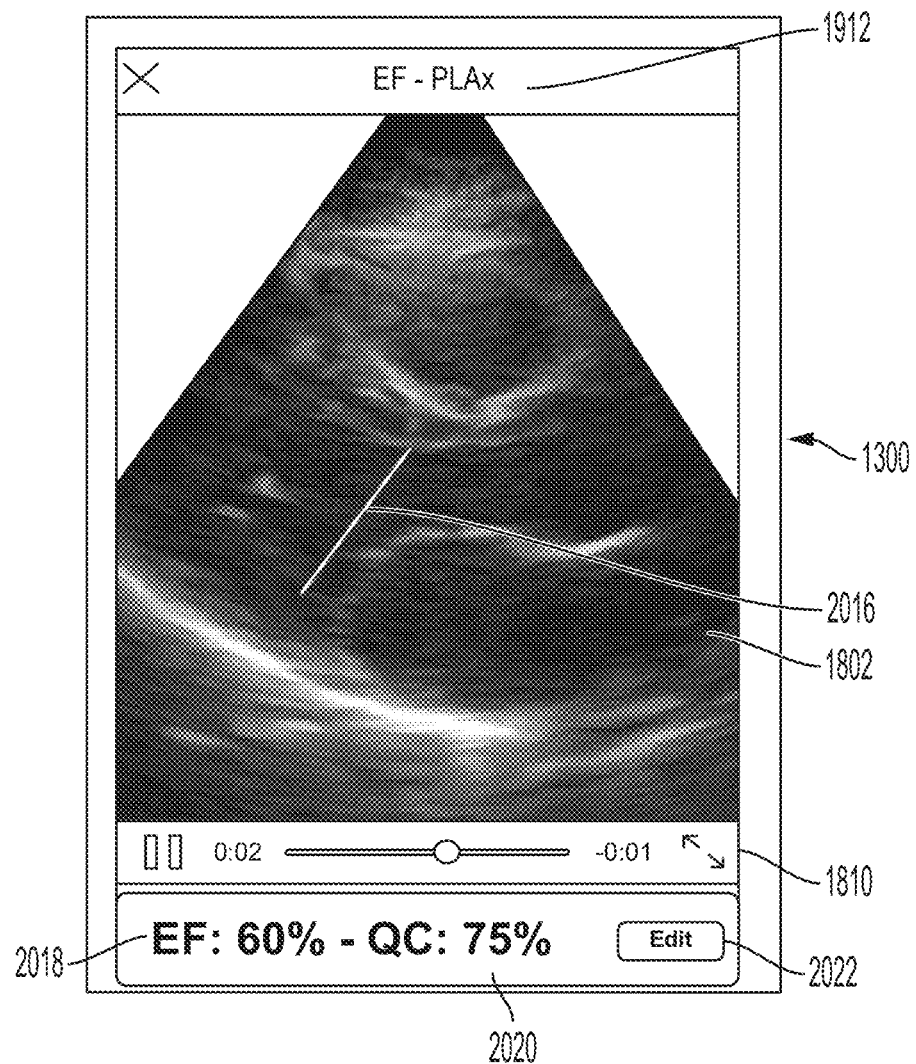
FIG. 20 illustrates another example of the GUI of FIG. 13, in accordance with certain embodiments described herein.

FIG. 20 shows another example of the GUI 1300 following an automatic measurement on a sequence of images, in accordance with certain embodiments described herein. In FIG. 20, the GUI 1300 includes a segmentation 2016 performed during the automatic measurement. For example, the segmentation 2016 in FIG. 20 may constitute identification of two landmark points, namely the endpoints of the long axis of the long ventricle in an image taken in parasternal long axis view of the heart, and formation of a line between the two landmark points. Other segmentations are also possible, such as left ventricle segmentation (i.e., determining foreground vs. background) in scans acquired from the apical four chamber view of the heart. The GUI 1300 further includes a result 2018 of the automatic measurement (in FIG. 20, an ejection fraction value, 60%) and the offline quality value 2020 calculated on the sequence of images (in FIG. 20, 75%). The GUI 1300 further shows an edit button 2022, selection of which may cause the computing device to enter a manual mode from which an operator may annotate/segment image(s) in the sequence of images, correct/alter automatically performed segmentations (e.g., segmentation 2016) and thereby manually perform measurements based on the sequence of images.

Figure 21:
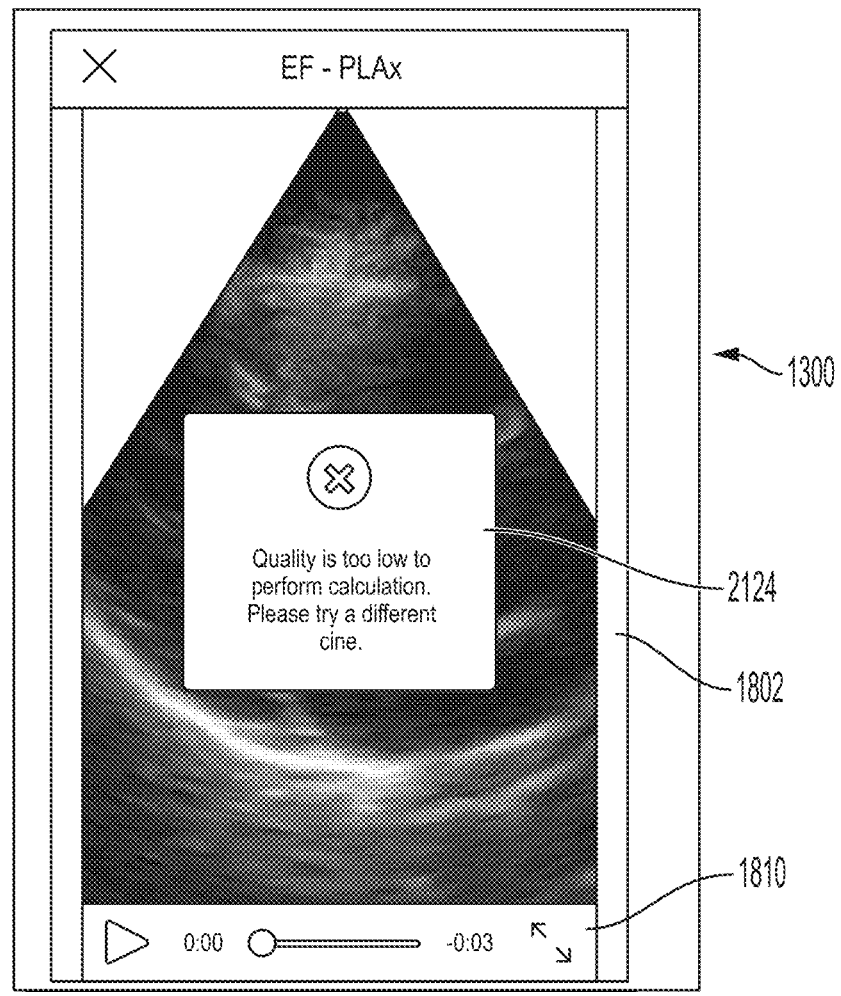
FIG. 21 illustrates another example of the GUI of FIG. 13, in accordance with certain embodiments described herein.

FIG. 21 shows another example of the GUI 1300 after selection of one of the measurement options 1804, 1806, or 1808, when the offline quality value calculated on the sequence of images does not exceed a threshold quality value, in accordance with certain embodiments described herein. The GUI 1300 shows an indicator 2124 indicating that the quality of the sequence of images is too low to perform the automatic measurement selected, and requesting that the operator choose another sequence of images for performing the automatic measurement.

Figure 22:
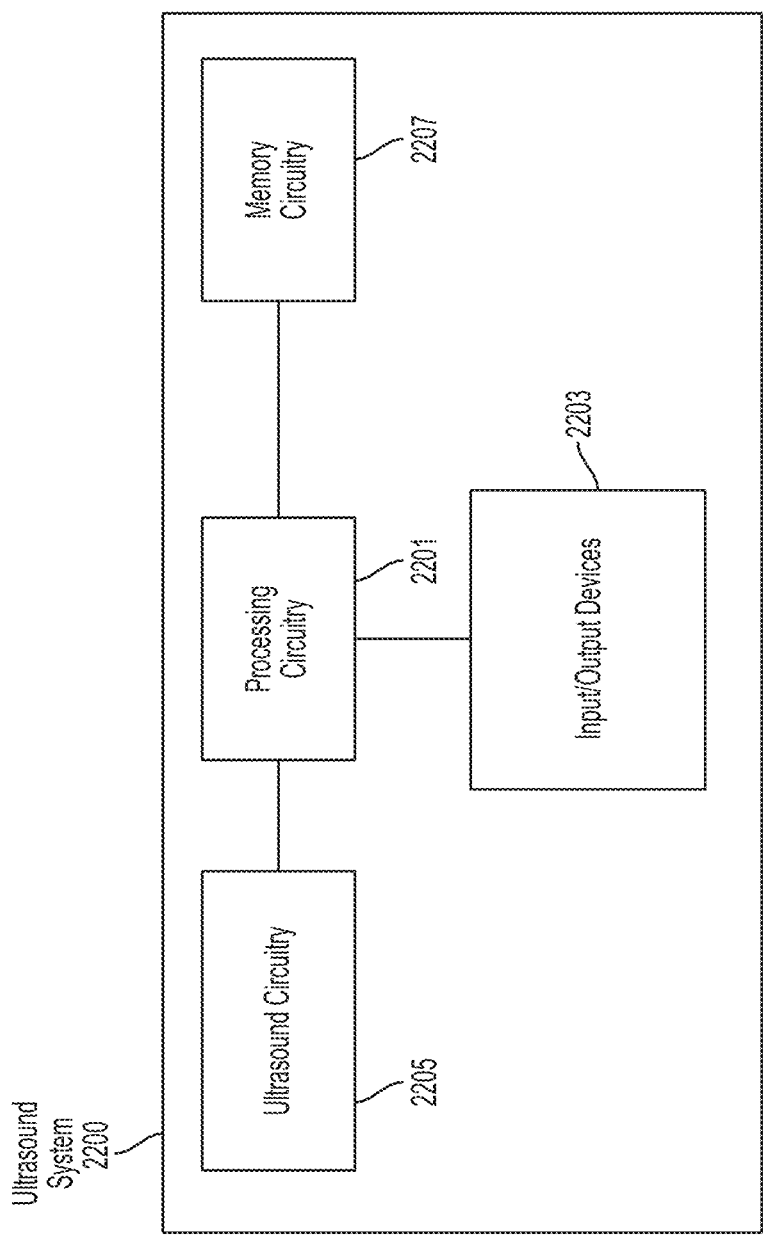
FIG. 22 shows a schematic block diagram illustrating aspects of an example ultrasound system upon which various aspects of the technology described herein may be practiced, in accordance with certain embodiments described herein.

FIG. 22 illustrates a schematic block diagram illustrating aspects of an example ultrasound system 2200 upon which various aspects of the technology described herein may be practiced. For example, one or more components of the ultrasound system 2200 may perform any of the processes described herein (such as the processes shown in FIGS. 1-3). As shown, the ultrasound system 2200 includes processing circuitry 2201, input/output devices 2203, ultrasound circuitry 2205, and memory circuitry 2207.

The ultrasound circuitry 2205 may be configured to generate ultrasound data that may be employed to generate an ultrasound image. The ultrasound circuitry 2205 may include one or more ultrasonic transducers monolithically integrated onto a single semiconductor die. The ultrasonic transducers may include, for example, one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 2205 (e.g., transmit circuitry, receive circuitry, control circuitry, power management circuitry, and processing circuitry) to form a monolithic ultrasound imaging device.

The processing circuitry 2201 may be configured to perform any of the functionality described herein (e.g., the processes 100, 200, and 300). The processing circuitry 2201 may include one or more processors (e.g., computer hardware processors). To perform one or more functions, the processing circuitry 2201 may execute one or more processor-executable instructions stored in the memory circuitry 2207. The memory circuitry 2207 may be used for storing programs and data during operation of the ultrasound system 2200. The memory circuitry 2207 may include one or more storage devices such as non-transitory computer-readable storage media. The processing circuitry 2201 may control writing data to and reading data from the memory circuitry 2207 in any suitable manner.

In some embodiments, the processing circuitry 2201 may include specially-programmed and/or special-purpose hardware such as an application-specific integrated circuit (ASIC). For example, the processing circuitry 2201 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network.

The input/output (I/O) devices 2203 may be configured to facilitate communication with other systems and/or an operator. Example I/O devices 2203 that may facilitate communication with an operator include: a keyboard, a mouse, a trackball, a microphone, a touch screen, a printing device, a display screen, a speaker, and a vibration device. Example I/O devices 2203 that may facilitate communication with other systems include wired and/or wireless communication circuitry such as BLUETOOTH, ZIGBEE, Ethernet, WiFi, and/or USB communication circuitry.

It should be appreciated that the ultrasound system 2200 may be implemented using any number of devices. For example, the components of the ultrasound system 2200 may be integrated into a single device. In another example, the ultrasound circuitry 2205 may be integrated into an ultrasound imaging device that is communicatively coupled with a computing device that includes the processing circuitry 2201, the input/output devices 2203, and the memory circuitry 2207.

Figure 23:
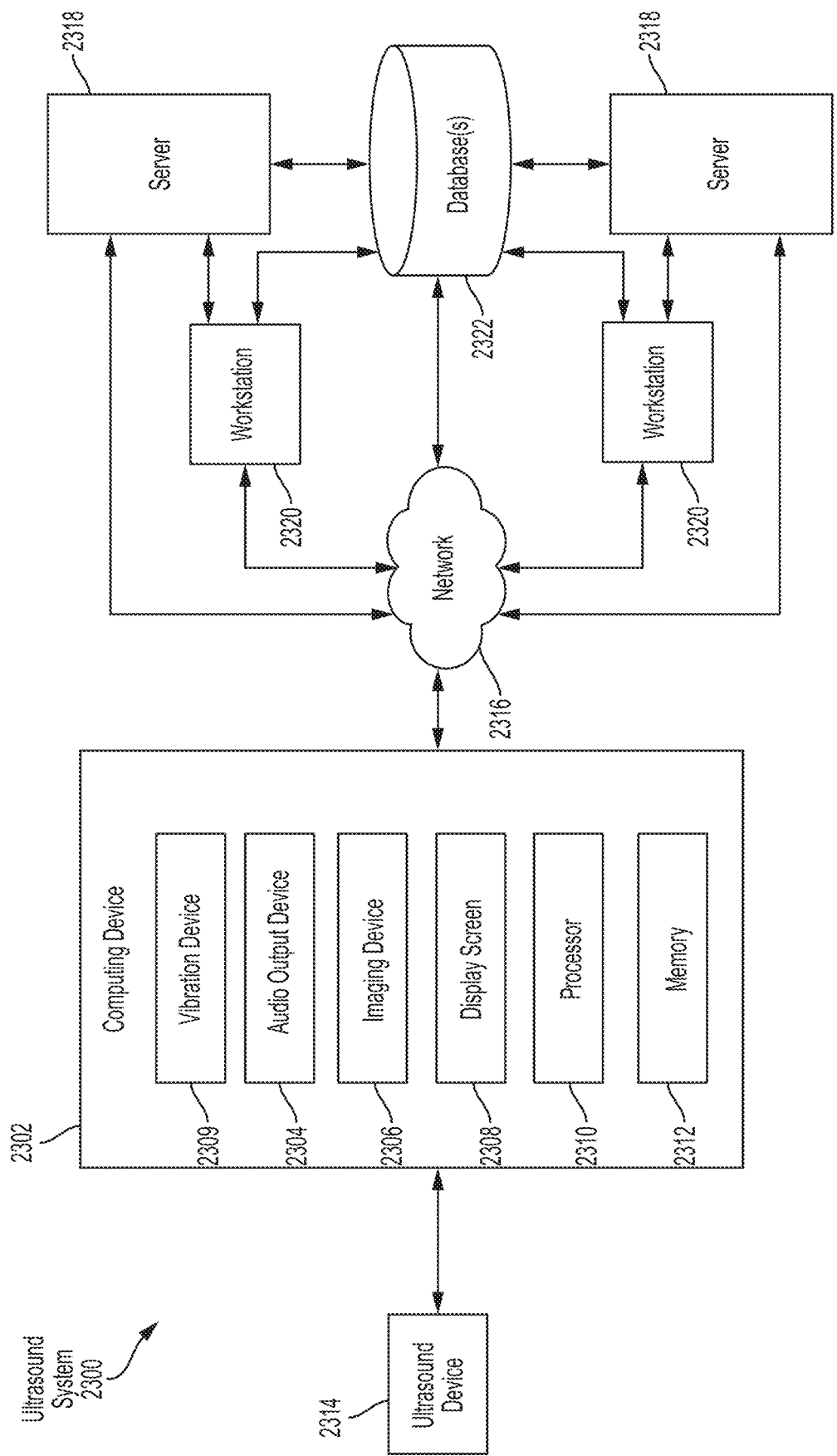
FIG. 23 shows a schematic block diagram illustrating aspects of another example ultrasound system upon which various aspects of the technology described herein may be practiced, in accordance with certain embodiments described herein.

FIG. 23 illustrates a schematic block diagram illustrating aspects of another example ultrasound system 2300 upon which various aspects of the technology described herein may be practiced. For example, one or more components of the ultrasound system 2300 may perform any of the processes described herein (such as the processes 100, 200, and 300). As shown, the ultrasound system 2300 includes an ultrasound imaging device 2314 in wired and/or wireless communication with a computing device 2302. The computing device 2302 includes an audio output device 2304, an imaging device 2306, a display screen 2308, a processor 2310, a memory 2312, and a vibration device 2309. The computing device 2302 may communicate with one or more external devices over a network 2316. For example, the computing device 2302 may communicate with one or more workstations 2320, servers 2318, and/or databases 2322.

The ultrasound imaging device 2314 may be configured to generate ultrasound data that may be employed to generate an ultrasound image. The ultrasound imaging device 2314 may be constructed in any of a variety of ways. In some embodiments, the ultrasound imaging device 2314 includes a transmitter that transmits a signal to a transmit beamformer which in turn drives transducer elements within a transducer array to emit pulsed ultrasonic signals into a structure, such as a patient. The pulsed ultrasonic signals may be backscattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data.

The computing device 2302 may be configured to process the ultrasound data from the ultrasound imaging device 2314 to generate ultrasound images for display on the display screen 2308. The processing may be performed by, for example, the processor 2310. The processor 2310 may also be adapted to control the acquisition of ultrasound data with the ultrasound imaging device 2314. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

Additionally (or alternatively), the computing device 2302 may be configured to perform any of the processes described herein, such as the processes 100, 200, and 300 (e.g., using the processor 2310). As shown, the computing device 2302 may include one or more elements that may be used during the performance of such processes. For example, the computing device 2302 may include one or more processors 2310 (e.g., computer hardware processors) and one or more articles of manufacture that include non-transitory computer-readable storage media such as the memory 2312. The processor 2310 may control writing data to and reading data from the memory 2312 in any suitable manner. To perform any of the functionality described herein, the processor 2310 may execute one or more processor-executable instructions stored in one or more non-transitory computer-readable storage media (e.g., the memory 2312), which may serve as non-transitory computer-readable storage media storing processor-executable instructions for execution by the processor 2310.

In some embodiments, the computing device 2302 may include one or more input and/or output devices such as the audio output device 2304, the imaging device 2306, the display screen 2308, and the vibration device 2309. The audio output device 2304 may be a device that is configured to emit audible sound such as a speaker. The imaging device 2306 may be configured to detect light (e.g., visible light) to form an image such as a camera. The display screen 2308 may be configured to display images and/or videos such as a liquid crystal display (LCD), a plasma display, and/or an organic light emitting diode (OLED) display. The vibration device 2309 may be configured to vibrate one or more components of the computing device 2302 to provide tactile feedback. These input and/or output devices may be communicatively coupled to the processor 2310 and/or under the control of the processor 2310. The processor 2310 may control these devices in accordance with a process being executed by the process 2310 (such as the processes 100, 200, and 300). Similarly, the processor 2310 may control the audio output device 2304 to issue audible instructions and/or control the vibration device 2309 to change an intensity of tactile feedback (e.g., vibration) to issue tactile instructions. Additionally (or alternatively), the processor 2310 may control the imaging device 2306 to capture non-acoustic images of the ultrasound imaging device 2314 being used on a subject to provide an operator of the ultrasound imaging device 2314 an augmented reality interface.

It should be appreciated that the computing device 2302 may be implemented in any of a variety of ways. For example, the computing device 2302 may be implemented as a handheld device such as a mobile smartphone or a tablet. Thereby, an operator of the ultrasound imaging device 2314 may be able to operate the ultrasound imaging device 2314 with one hand and hold the computing device 2302 with another hand. In other examples, the computing device 2302 may be implemented as a portable device that is not a handheld device such as a laptop. In yet other examples, the computing device 2302 may be implemented as a stationary device such as a desktop computer.

In some embodiments, the computing device 2302 may communicate with one or more external devices via the network 2316. The computing device 2302 may be connected to the network 2316 over a wired connection (e.g., via an Ethernet cable) and/or a wireless connection (e.g., over a WiFi network). As shown in FIG. 23, these external devices may include servers 2318, workstations 2320, and/or databases 2322. The computing device 2302 may communicate with these devices to, for example, off-load computationally intensive tasks. For example, the computing device 2302 may send an ultrasound image over the network 2316 to the server 2318 for analysis (e.g., to identify an anatomical feature in the ultrasound) and receive the results of the analysis from the server 2318. Additionally (or alternatively), the computing device 2302 may communicate with these devices to access information that is not available locally and/or update a central information repository. For example, the computing device 2302 may access the medical records of a subject being imaged with the ultrasound imaging device 2314 from a file stored in the database 2322. In this example, the computing device 2302 may also provide one or more captured ultrasound images of the subject to the database 2322 to add to the medical record of the subject. For further description of ultrasound imaging devices and systems, see U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application) and published as U.S. Pat. Pub. 2017/0360397 A1.

Aspects of the technology described herein relate to the application of automated image processing techniques to analyze images, such as ultrasound images. In some embodiments, the automated image processing techniques may include machine learning techniques such as deep learning techniques. Machine learning techniques may include techniques that seek to identify patterns in a set of data points and use the identified patterns to make predictions for new data points. These machine learning techniques may involve training (and/or building) a model using a training data set to make such predictions. The trained model may be used as, for example, a classifier that is configured to receive a data point as an input and provide an indication of a class to which the data point likely belongs as an output.

Deep learning techniques may include those machine learning techniques that employ neural networks to make predictions. Neural networks typically include a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input, for example, to weight some inputs higher than others. Example transfer functions that may be employed include step functions, piecewise linear functions, and sigmoid functions. These neurons may be organized into a plurality of sequential layers that each include one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may include a set of example inputs and an answer associated with each input. For example, the training data may include a plurality of ultrasound images or sets of raw acoustical data that are each labeled with an anatomical feature that is contained in the respective ultrasound image or set of raw acoustical data. In this example, the ultrasound images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

Once the training data has been created, the training data may be loaded to a database (e.g., an image database) and used to train a neural network using deep learning techniques. Once the neural network has been trained, the trained neural network may be deployed to one or more computing devices. It should be appreciated that the neural network may be trained with any number of sample patient images. For example, a neural network may be trained with as few as 7 or so sample patient images, although it will be appreciated that the more sample images used, the more robust the trained model data may be.

Figure 24:
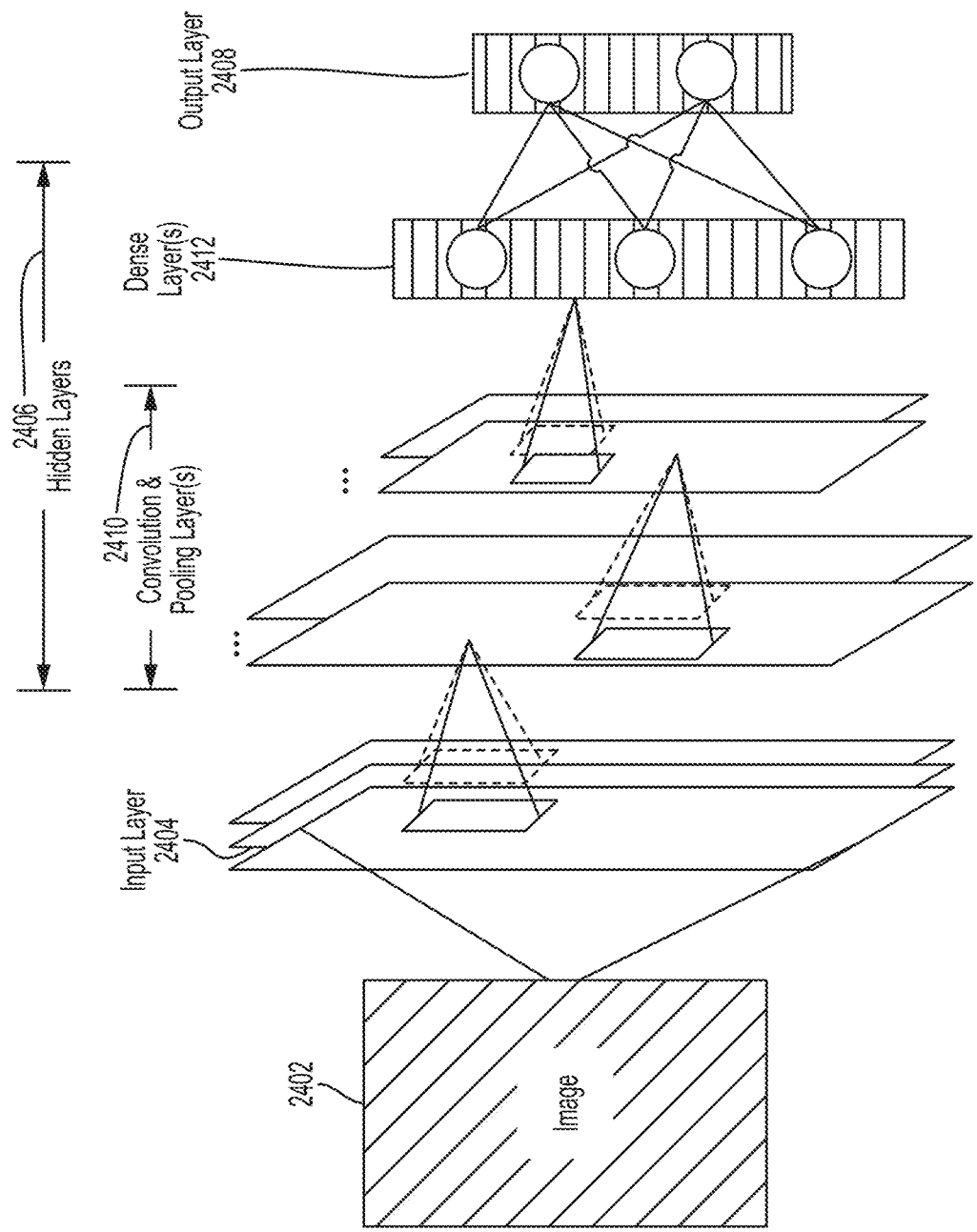
FIG. 24 illustrates an example convolutional neural network that is configured to analyze an image, in accordance with certain embodiments described herein.

In some applications, a neural network may be implemented using one or more convolution layers to form a convolutional neural network. An example convolutional neural network is shown in FIG. 24 that is configured to analyze an image 2402. As shown, the convolutional neural network includes an input layer 2404 to receive the image 2402, an output layer 2408 to provide the output, and a plurality of hidden layers 2406 connected between the input layer 2404 and the output layer 2408. The plurality of hidden layers 2406 includes convolution and pooling layers 2410 and dense layers 2412.

The input layer 2404 may receive the input to the convolutional neural network. As shown in FIG. 24, the input the convolutional neural network may be the image 2402. The image 2402 may be, for example, an ultrasound image.

The input layer 2404 may be followed by one or more convolution and pooling layers 2410. A convolutional layer may include a set of filters that are spatially smaller (e.g., have a smaller width and/or height) than the input to the convolutional layer (e.g., the image 2402). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 2410 may be followed by dense layers 2412. The dense layers 2412 may include one or more layers each with one or more neurons that receives an input from a previous layer (e.g., a convolutional or pooling layer) and provides an output to a subsequent layer (e.g., the output layer 2408). The dense layers 2412 may be described as "dense" because each of the neurons in a given layer may receive an input from each neuron in a previous layer and provide an output to each neuron in a subsequent layer. The dense layers 2412 may be followed by an output layer 2408 that provides the output of the convolutional neural network. The output may be, for example, an indication of which class, from a set of classes, the image 2402 (or any portion of the image 2402) belongs to.

It should be appreciated that the convolutional neural network shown in FIG. 24 is only one example implementation and that other implementations may be employed. For example, one or more layers may be added to or removed from the convolutional neural network shown in FIG. 24. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

For further description of deep learning techniques, see "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A method comprising calculating, during imaging, using a computing device in communication with an ultrasound device, a quality of a sequence of images collected by the ultrasound device during the imaging,
wherein the calculating of the quality of the sequence of images comprises:
calculating a quality of each respective image in the sequence of images, and
calculating an arithmetic mean of the quality of each respective image in the sequence of images to produce the quality of the sequence of images, and
wherein the calculating of the quality of each respective image in the sequence of images comprises, for each respective image in the sequence of images:
calculating a clinical use metric comprising a probability that a medical professional would use the respective image for clinical evaluation,
calculating an automated analysis metric comprising a quality of an automated analysis performed on the respective image, and
calculating a geometric mean of the clinical use metric and the automated analysis metric to produce the quality of the respective image.

2. The method of claim 1, further comprising generating for display, during the imaging, an indicator of the quality of the sequence of images.

3. The method of claim 2, further comprising:
receiving a newest image collected during the imaging;
removing an oldest image from the sequence of images and adding the newest image to the sequence of images to form a new sequence of images;
calculating, during the imaging, a quality of the new sequence of images; and
generating for display, during the imaging, an indicator of the quality of the new sequence of images to replace the indicator of the quality of the sequence of images.

4. The method of claim 2, further comprising generating for display instructions for moving the ultrasound device performing the imaging.

5. The method of claim 4, wherein the generating for display of the instructions for moving the ultrasound device performing the imaging comprises generating for display the instructions simultaneously with generating for display the indicator of the quality of the sequence of images.

6. The method of claim 4, wherein the generating for display of the instructions for moving the ultrasound device performing the imaging comprises generating for display the instructions prior to generating for display the indicator of the quality of the sequence of images.

7. The method of claim 1, wherein the sequence of images comprises a sequence of images collected during a fixed period of time prior to calculating the quality of the sequence of the images.

8. The method of claim 1, wherein the sequence of images comprises a fixed number of images collected prior to calculating the quality of the sequence of the images.

9. The method of claim 1, wherein the calculating of the quality of the sequence of images comprises analyzing the sequence of images using deep learning techniques.

10. The method of claim 9, wherein the calculating of the quality of the images comprises providing at least one image in the sequence of images as an input to a statistical model.

11. The method of claim 10, wherein the calculating of the quality of the images comprises using the statistical model to obtain an output that is indicative of the quality of the at least one image.

12. The method of claim 1, further comprising generating for display, during the imaging, an indicator of an acceptability of the sequence of images.

13. The method of claim 1, wherein the generating for display of the indicator of the quality of the sequence of images comprises:
generating for display a frame having a first end and a second end and
generating for display a bar within the frame that extends from the first end towards the second, wherein a length of the bar relative to the frame is proportional to the quality of the sequence of the images.

14. The method of claim 13, further comprising generating for display, during the imaging, an indicator of an acceptability of the sequence of images, wherein the indicator of the acceptability of the sequence of images comprises an indicator of a threshold quality such that a distance from the first end to the indicator of the threshold quality relative to the length of the bar is proportional to the threshold quality.

15. The method of claim 1, further comprising:
storing one or more images in the sequence of images in a volatile memory;
deleting an oldest image from the one or more images stored in the volatile memory;
adding a newest image to the one or more images stored in the volatile memory;
determining whether a quality of the one or more images stored in the volatile memory exceeds a threshold quality; and
based on a determination that the quality of the one or more images stored in the volatile memory exceeds the threshold quality, obtained from the determining, transferring the one or more images stored in the volatile memory from the volatile memory to a non-volatile memory.

16. A method for performing automatic measurements on a sequence of images collected by an ultrasound device, the method comprising:
receiving, using a computing device, a trigger to perform an automatic measurement on the sequence of images;
calculating a quality of the sequence of images;
determining whether the quality of the sequence of images exceeds a threshold quality; and
based on a determination that the quality of the sequence of images exceeds the threshold quality, obtained from the determining, performing the automatic measurement on the sequence of images,
wherein the calculating of the quality of the sequence of images comprises:
calculating a quality of each respective image in the sequence of images to produce a plurality of qualities, and
calculating a fixed percentile of the plurality of qualities to produce the quality of the sequence of images, and
wherein the calculating of the quality of each respective image in the sequence of images comprises, for each respective image in the sequence of images:
calculating a clinical use metric comprising a probability that a medical professional would use the respective image for clinical evaluation, calculating an automated analysis metric comprising a quality of an automated analysis performed on the respective image, and calculating a geometric mean of the clinical use metric and the automated analysis metric to produce the quality of the respective image.

17. The method of claim 16, further comprising:

based on a determination that the quality of the sequence of images does not exceed the threshold quality, obtained from the determining, generating for display an indicator that the quality of the sequence of images does not exceed the threshold quality.

18. The method of claim 16, further comprising:

based on a determination that the quality of the sequence of images does not exceed the threshold quality, obtained from the determining, entering a manual mode in which an operator may perform a manual measurement on the sequence of images.

19. A method for performing automatic measurements on a sequence of images collected by an ultrasound device, the method comprising:

receiving, using a computing device, a trigger to perform an automatic measurement on the sequence of images;

calculating a quality of the sequence of images;

determining whether the quality of the sequence of images exceeds a threshold quality; and based on a determination that the quality of the sequence of images exceeds the threshold quality, obtained from the determining, performing the automatic measurement on the sequence of images, wherein the automatic measurement comprises automatic measurement of an ejection fraction, and wherein the calculating of the quality of the sequence of images comprises:

calculating a first quality comprising a minimum of a first plurality of qualities of a first plurality of images, wherein the first plurality of images comprises a first image corresponding to end-diastole and one or more images that are temporally adjacent to the first image in the sequence of images, calculating a second quality comprising a minimum of a second plurality of qualities of a second plurality of images, wherein the second plurality of images comprises a second image corresponding to end-systole and one or more images that are temporally adjacent to the second image in the sequence of images, calculating a quality of each respective image in the sequence of images to produce a third plurality of qualities, calculating a fixed percentile of the third plurality of qualities to produce a third quality, and selecting the quality of the sequence of images as a minimum of the first quality, the second quality, and the third quality.

\* \* \* \* \*

UNITED STATES PATENT AND TRADEMARK OFFICE
CERTIFICATE OF CORRECTION

PATENT NO. : 10,628,932 B2
APPLICATION NO. : 16/172076
DATED : April 21, 2020
INVENTOR(S) : Alex Rothberg et al.

Page 1 of 1

It is certified that error appears in the above-identified patent and that said Letters Patent is hereby corrected as shown below:

In Claim 13, at Column 28, Line 12, delete "second end and" and replace it with --second end, and--.

Signed and Sealed this
Tenth Day of November, 2020

Andrei Iancu
*Director of the United States Patent and Trademark Office*